United States Patent
Karp

(10) Patent No.: US 7,790,177 B2
(45) Date of Patent: Sep. 7, 2010

(54) IMMUNIZING COMPOSITIONS COMPRISING RECOMBINANT ATTENUATED SELF-REPLICATING VIRAL RNA REPLICONS ENCODING AN EPITOPE OBTAINED FROM THE HIV-1 MATRIX PROTEIN MYRSTATE BINDING SITE

(76) Inventor: Nelson M. Karp, 4837 Kempsville Greens Pkwy., Virginia Beach, VA (US) 23462

( * ) Notice: Subject to any disclaimer, the term of this patent is extended or adjusted under 35 U.S.C. 154(b) by 0 days.

(21) Appl. No.: 12/229,865

(22) Filed: Aug. 27, 2008

(65) Prior Publication Data
US 2009/0028890 A1 Jan. 29, 2009

Related U.S. Application Data

(63) Continuation of application No. 10/971,229, filed on Oct. 22, 2004, now Pat. No. 7,611,712.

(60) Provisional application No. 60/513,827, filed on Oct. 23, 2003.

(51) Int. Cl.
| A61K 39/12 | (2006.01) |
| A61K 39/21 | (2006.01) |
| A61K 39/193 | (2006.01) |
| C07H 21/04 | (2006.01) |

(52) U.S. Cl. ............... 424/199.1; 424/188.1; 424/218.1; 536/23.72

(58) Field of Classification Search ........................ None
See application file for complete search history.

(56) References Cited

U.S. PATENT DOCUMENTS

| 5,443,828 | A | 8/1995 | Kang et al. |
| 5,576,421 | A | 11/1996 | Saito et al. |
| 5,817,512 | A | 10/1998 | Morrow et al. |
| 6,627,197 | B2 | 9/2003 | Keener et al. |
| 7,446,189 | B1 * | 11/2008 | Weiner et al. ............... 536/23.4 |

FOREIGN PATENT DOCUMENTS

WO WO 2004002415 1/2004

OTHER PUBLICATIONS

Mata, M., et al., 2001, Evaluation of a recombinant *Listeria monocytogenes* expressing an HIV protein that protects mice against viral challenge, Vaccine 19:1435-1445.*
Fleeton, M. N., et al., 2001, Self-replicative RNA vaccines elicit protection against influenza A virus, respiratory syncytial virus, and a tickborne encephalitis virus, J. Infect. Dis. 183:1395-1398.*
Sasaki, S., et al., 1998, Induction of systemic and mucosal immune responses to human immunodeficiency virus type 1 by a DNA vaccine formulated woth QS-21 saponin adjuvant via intramuscular and intranasal routes, J. Virol., 72(6):4931-4939.*
Becker, P.D., et al., The HIV-1 Matrix Protein p17 can be efficiently delivered by intranasal route in mice using the TLR 2/6 aginist MALP-2 as mucosal adjucant.

Frankel, F.R., et al., 1995, Induction of cell-mediated immune response to human immununodeficiency virus type 1 Gag protein by using *Listeria monocytogenes* as a live vaccine vector, J. Immunol, 155;4775-4782.
Miller, M. A., et al., 1996, Protective immunity to *Listeria monocytogenes* elicited by immunization with heat-killed *Listeria* and IL-12, Annals N.Y. Acad. Sci. 797:207-227 (abstract provided).
Human Retoviruses and Aids 1999: A compilation and analysis of nucleic acid and sequesnces, Kulken, C.L., et al., eds., Theoretical Biology and Biophysics Group, Los Alamos National Laboratory, Los Alamos, NM, HIV/SIV Gag sequence compendium, pp. 332-341.
Hermida-Matsumoto Luz, et al.: "Human Immunodeficiency Virus Type 1 Protease Triggers a Myristoyl Switch That Modulates Membrane Binding of Pr55gag and p17MA" Journal of Virology, vol. 73, No. 3, Mar. 1999, pp. 1902-1908, XP002485536, ISSN: 0022-538X.
Kiernan, R. E., et al.: Reversion of a Human Immonodeficiency Virus Type 1 Matrix Mutating Affecting Gag Membrane Binding, Endogenous Reverse Transcriptase Activity, and Virus Infectivity: Journal of Virology Jun. 1999, vol. 73, No. 6, Jun. 1999, pp. 47284737, XP002485535.
Pinter, C., et al.: "Interference with Complement Regulatory Molecules as a Possible Therapeutic Strategy in HIV Infection" Expert Opinion on Investigational Drugs Feb. 2000 vol. 9, No. 2, Feb. 1, 2000, pp. 199-205, XP002484637.
Aiken, C., et al.: "Inside-out Regularion of HIV-1 Particle Fusion," Progeam and Abstract of the 10th Conference on Retrovirus and Opportunitistic Infections, Boston, MA USA Abstract 17 (Feb. 10-14, 2003).
Aroeti, Benjamin, et al.: "Mutational and Secondary Structural Analysis of the Basolateral Sortin Signal of the Polymetic Immmunoglobulin Receptor", J. Cell Biology, vol. 123, No. 5, 1149-1160 (1993).
Ara, Yuki, et al.: "Zymozan enhances the immune response to DNA vaccine for human immunodeficiency virus type-1 through the activation of complement system" Immunology 103:98-105 (2001), Japan.
Aslam, Mohammed, et al.: "Folded Back Solustion Structure of Monomeric Factor H of Human Compement by Synchrotron X-ray and Neutron Scattering, Analytical Ultracentrifudation and Constrained Molecular Modeling," Molecular Biology, vol. 309, pp. 1117-1138 (2001).
Ault, Bettina, et al.: "Human Factor H. Deficiency," Biology Chemistry, vol. 272, #40, pp. 25168-25175 (1997) USA.
Black, T.K., et al. "Identification of a Halperin Binding Domain in the Seventh Short Consensus Repeat of Complement Factor H" Immunology, vol. 157. Iss 12 pp. 5422-5427 (1996).
Braaten, D., et al., "Cyclophilin A regulates HIV-1 infectivity, as demonstrated by gene targeting of human T'cells," The EMBO Journal, vol. 20, No. 6. pp. 1300-1309, 2001.

(Continued)

Primary Examiner—Jeffrey S. Parkin
(74) Attorney, Agent, or Firm—Williams Mullen; Kelly J. Hollowell

(57) ABSTRACT

The present invention relates to an immunogenic composition. More particularly, the present invention is a composition directed to eliciting an immune response to at least one covalent binding site of myristate (SEQ ID NOS: 1-3) on the HIV matrix protein. The present invention contemplates three categories of embodiments: protein or protein fragments (SEQ ID NO: 1), messenger RNA, or DNA/RNA (SEQ ID NOS:2-3). DNA/RNA compositions may be either naked or recombinant. The present invention further contemplates use with a variety of immune stimulants.

8 Claims, 8 Drawing Sheets

OTHER PUBLICATIONS

Burger, R., et al., "Activation of the alternative pathway of complement: efficient fluid-phase amplification by blockade of the regulatory complement protein B1H through sulfated polyanions," European J. Immunology, vol. 11, pp. 291-293 (1981).

Doepper, Susi, et al., "Complement Receptors to HIV Infection," Current Melecular Medicine, vol. 2, Iss 8. pp. 703-711 (2002).

Burger, R., et al., "Dextran Sulphate: a Synthetic Activator of C3 via the Alternative Pathway," Immunology, vol. 29. pp. 549-554 (1975).

Burger, R., et al., "Insoluble polyanions as activators of both pathways of complement," Immunology 33:827-837 (1977).

Chan, D.C., et al., "Core Structure of gp41 from the HIV Envelope Glycoprotein" Cell, vol. 89, Issue 2, pp. 263-273 (Apr. 18, 1997).

Chen, Chien-Hung, et al., "Enhancement of DNA Vaccine Potency by Linkage of Antigen Gen to an HSP70 Gene," Cancer Research 60: 1035-1042 (Feb. 15, 2000).

Cheng, Wen-Fang, et al., "Tumor-specific immunity and antiangiogenisus generated by a DNA vaccine encoding calreticulin linked to a tumor antigen," Journal of Clinical Investigation, vol. 108, No. 5, 669-678 (Sep. 2001).

Hung-Chien-Fu, et al., "Enhancing Major Histocompatibility Complex Class 1 Antigen Presentation by Targeting Antigen to Centrosomes," Cancer Research 63: 2393-2398, (May 15, 2003).

Cohen, P. T., The AIDS Knowledge Base, 15-18, 21 (3rd ed. 1999).

Cummins, Melissa, et al., New Research Uncovers Potential for More Effective Anti-HIV Therapies: Essential Role of Cyclophilin, Novel Non-Mutable Drug Target Discovered, PR NewsWire 1996.

Dierich, M. P., et al., "HIV and human complement: mechanisms of interaction and biological implications," Immunology Today,vol. 14, Iss 9, pp. 435-440 (1993).

Discipio, R. G., "Ultrstructures and interactions of compelement factors H and I," J. Immunology, vol. 149, ISS 8, pp. 2592-2599 (1992).

Perron, D.T., et al., "Activation of the alternative complement pathway due to resistence of zymosan-bound amplification convertase to endogenous regulatory mechanisms," Proc. Natl. Acad. Sci. vol. 74, No. 4 pp. 1683-1687 (Apr. 1977).

Feifel, Elisabeth, et al., "Polymorphism and deficiency of human factor H-related proteins p39 and p37," Immunogenetics, vol. 36, pp. 104-109 (1992).

Fishelson, Z., et al., C3 Convertase of Human Complement: Enhanced Formation and Stability of the Enzyme generated with Nickel instead of Mafnesium,: J. of Immun., vol. 129, No. 6, pp. 2603-2607 (Dec. 1982).

Forrest, Bruce D., et al., "Effect of Parenteral Immunization on the Intestinal Immune Response to Salmonella typhy Ty21a," Infection and Immunity, col. 60, No. 2, pp. 465-471 (Feb. 1992(.

Franke, E.K., et al., "Chaperoning a pathogen," Nature, 372 (6504) 319-20 (Nov. 24, 1994).

Franke, E.K., et al., "Specific Incorporation of Cyclophilin A into HIV-1 Virions," Nature, 372(6504: 359 (Nov. 24, 1994).

Friese, M.A., "FHL-1/reconectin and factor H: two human complement regulators which are encoded by the same gene are differently expressed and regulated," Molecular Immunology, vol. 36, pp. 809-818 (1999).

Gardner, William D., "Identification of a major human serum DNA-binding protein as BIH of the alternative pathway of complement activation", Biochemical and Biophysical Research Communications, vol. 94, pp. 61-67 (1980).

Gasque, P., "Expression of complement components of the alternative pathway by glioma cell lines", Immunology, 149:1381-87 (1992).

Giannakis, Eleni, et al., "Multiple ligand binding sites on domain seven of human complement factor H", Int'l. Immunopharmacology, vol. 1, Issue 3, pp. 433-443 (2001).

Goudsmit, J., Immunodominant B-Cell epitopes of the HIV-1 envelope recognized by infected and immunized hosts, AIDS, vol. 2 (Suppl 1); S41-S45 (1988).

Gowda, D.C., et al., "Immunoreactivity and Function of Oligosaccharides in Cobra Venom Factor", J. of Immun., vol. 152, Issue 6, pp. 2977-2986 (Dec. 1993).

Harrison, Stephen, Howard Hughes Medical Institute, Remarks for Institute News titled "HIV's Deep Picket May Reveal Vulnerability; Seeing the Structure of the Viral Protein gp41 suggested experimental design" (Sep. 28, 1999); Internet: www.hhmi.org/news/gp41.html.

Haurum, John, "Complement activation upon binding of mannan-binding protein to HIV envelope glycoproteins", AIDS, vol. 7 (10), pp. 1307-1313 (1993).

Hellwage, J., "Functional Properties of complement factor H-related proteins FHR-3 and FHR-4: binding to the C3d region of C3b and differential regulation by Heparin", FEBS Lett. 426(3); 345-352 (Dec. 3, 1999).

Hoffman, Ronald, Hemotology Basic Principles and Practice, Ch. 36, pp. 640-651; pp. 651-667; Ch. 39, pp. 686-701 ($3^{rd}$ ed. 2000).

Hogan, Christine M. et al., "Host Determinants in HIV Invention and Disease", Ann. Intern. Med. 13(10); 978-996 (2001).

Hughson, F.M., "Enveloped viruses: A common mode of membrane fusion?" Current Biology 7(9): R565-R569 (1997).

Hughes, Huw, "Bacterial Vectors for Vaccine Delivery", Designer Vaccines: Principles for Successful Prophylaxis, Ch. 2, 8, pp. 151-178 (1998).

Joiner, K.A., "Complement Evasion by Bacteria and Parasites", Ann. Rev. Microbiol., vol. 42, pp. 201-230 (1988).

Johnston, Margaret, et al., "Progress in HIV vaccine development", Current Opinion in Pharmacology, 1:50-510 (2001).

Jokiranta, T., "Analysis of the recognition mechanism of the alternative pathway of complement by monoclonal anti-factor H antibodies: evidence for multiple interactions between H and surface bound C3b", FEBS Lett., 393:297-302 (Sep. 16, 1996).

Jokiranta, T., "Each of the Three Binding Sites on Complement Factor H Interacts with a Distinct Site on C3b", J. of Biological chemistry, vol. 275, #36, 27657-27662 (Sep. 8, 2000).

Kaplan, G., et al., "Construction and Characterization of Poliovirus Subgenomic Replicons", J, Virol. 62(5): 1687-96 (May 1988).

Kaufmann, Stefan H.E., Concepts in Vaccine Development, Ch. 2, 3, 7 (1996).

Keren, David F., et al.; "Combined Parenteral and Oral Immunization Results in an Enhanced Mucosal Immunoglobulin A Response to Shigella Flexeri", Infect. Immun. 56:910-915 (1988).

Kirkitadze, Marina, et al.; "Structure and flexibility of the multiple domain proteins that regulate complement activation", Immun. Rev., vol. 180, pp. 146-161 (2001).

Kitamura, N. et al., "Primary structure, gene organization and polypeptide expression of poliovirus RNA", Nature 291: 547-553 (1981).

Kiyono, Hiroshi, et al., Mucosal Vaccines, Prospects for Induction of Mucosal Immunity by DNA Vaccines, Ch. 8, pp. 119, 127 (1996).

Kock, Michael A., et al., "Structure and function of recombinant Cobra Venom Factor", J. of Biol. Chemistry, vol. 279, pp. 30836-30843 (2004).

Lachmann, P.J., "The Influence of C3b Inactivator (KAF) Concentration on the Ability of Serum to Support Complement Activation", Clin. Exp. Immonol., vol. 21, pp. 109-114 (1975).

Lee, Young-Min, et al., "A Bipartite Membrane-Binding Signal in the Human Immunodeficiency Virus Type 1 Matrix Protein is Required for the Proteolytic Processing of Gag Precursors in a Cell Type-Dependent Manner", J. of Virology, pp. 99061-99068 (Nov. 1998).

Legendre, C., et al., "Mechanisms of opsonized HIV entry in normal B lymphoytes", FEBS Lett. 381-227-232 (1996).

Levinson, Warren, et al., Medical Microbiology & Immunology, Chapter 58, pp. 363-381, 401($7^{th}$ ed. 2002).

Levy, J.A., "Pathogenesis of Human Immunodeficiency Virus Infection", Microbiol. Rev. 57(1): 183-289 (1993).

Lewis, P.J., et al., "Altering the Cellular Location of an Antigen Expressed by a DNA-Based Vaccine Modulates the Immune Response"; Journal of Virology, 73(12); 10214-10223 (Dec. 1999).

Liang, J.F., et al., "A Less Toxic Heparin Antagonist-Low Molecular Weight Protamine", Biochemistry, vol. 68(1); 116-120 (2003).

Maillet, Francoise, et al., "Heparin Prevents Formation of the Human C3 Amplification Convertase by Inhibiting the Binding Site for B on C3b", Molecular Immun., vol. 20(12): 1401-1404 (1983).

Maillet, Francoise, et al., "Structure-function Relationships in the Inhibitory Effect of Heparin on Complement Activation; Independency of the Anti-coagulant and Anti-complementary sites on the Heparin Molecule", Molecular Immun., vol. 25(9): 917-923 (1988).

Mcrae, Jennifer, et al.; "Human Factor H-related Protein 5 (FHR-5)", Biological Chemistry, vol. 276 (9): 6747-6754 (2001).

Mcmichael, Andrew, J., et al., "Cellular Immune responses to HIV", Nature, 410:980-987 (Apr. 19, 2001).

Meri, Seppo, et al.; "Discrimination between activators and nonactivators of the alternative pathway of complement; Regulation via a sialic acid/polyanion binding site on factor H", Proc. Natl. Acad. Sci., USA, vol. 87, pp. 3982-3986 (May 1990).

Michalek, Michael T., et al., "Inhibition of the Alternative Pathway of Human.Complement by Structural Analogues of Sialic Acid", J. Immunology, vol. 140, pp. 1588-1594 (1988).

Morrow, W. J., et al., "Circulating Immune Complexes in Patients with Acquired Immune Deficiency Syndrome Contain the AIDS-Associated Retrovirus", Clin. Immunol. and Immunopathol., 40:515-24 (1986).

Nicholl, Desmond, An Introduction to Genetic Engineering, Ch. 3, 5 (2nd Ed. 2002).

Nilsson, U.R., et al., J. Exp. Med. 122: 277-289 (1965).

Ono, Akira, et al., "Binding of Human Immunodeficiency Virus Type 1 Gag to Membrane: Role of the Matrix Amino Terminus", J. of Virology, vol. 73, No. 5, pp. 4136-4144 (May 1999).

Pangburn, M.K., "Analysis of Recognition in the Alternative Pathway of Complement: Effect of Polysaccharide Size", J. of Immunol., vol. 142 (8); 2766-2770 (Apr. 1989).

Pangburn, M.K., "Molecular Mechanisms of Target Recognition in an Ionate Immune System: Interactions Among Factor H, C3b, and Target in the Alternative Pathway of human Complements: effect of Polysaccharide Size", J. of Immunol., vol. 164; pp. 4742-4751 (2000).

Pantaleo, G., et al., "Studies in Subjects With Long-Term Nonprogressive Human Immunodeficiency Virus Infection", N. Engl. J. Med., vol. 332, No. 4, 332: 209-16 (1995).

Parham, Peter, The Immune System, Ch. 7, 12 ($2^{nd}$ Ed. 2004).

Paul, William E.; Fundamental Immunology, pp. 967-994 ($4^{th}$ ed. 1999).

Printer, Claudia, et al., "HIV Glycoprotein 41 and Complement Factor H interact with Each other and Share Functional as Well as Antigenic Homology", AIDS Research in Human Retroviruses, vol. 11(8): 971-80 (Nov. 8, 1995).

Printer, Claudia, et al., Direct Interaction of Complement Factor H Interact with the C1 Domain of HIV Type 1 Glycoprotein AIDS Research and Human Retroviruses, vol. 11(5): 577-588 (Nov. 8, 1995).

Porter, Donna C., et al., Encapsidation of Poliovirus Replicons Encoding the Complete Human Immunodeficiency Virus type gag Gene by Using a Complementation System Which Provides the P1 Capsid Protein in trans, Journal of Virology, vol. 69(3); 1548-1555 (Mar. 1995).

Presanis, J.S., et al., "Biochemistry and genetics of mannan-binding lectin (MBL)", Biochemical Society Transactions, vol. 31, Part 4, pp. 748-752 (2003).

Procaccia, S. et al., "Rheumatoid factors and circulating immune complexes in HIV infected individuals", AIDS, vol. 5(12): 1441 (1991).

Racaniello, V.R., et al., "Molecular cloning of poliovirus cDNA and determination of the complete nucleotide sequence of the viral genone", Proceedings of the National Academy of Sciences, USA, 78(8); 4887-4891; (Aug. 1981).

Reisenger, E.C., et al., "Complement-mediated enhancement of HIV-1 infection of the monoblastoid cell line U9317", AIDS, vol. 4, pp. 961-965 (1990).

Ren, R., et al., "Human Poliovirus Receptor Gene Expression and Poliovirus Tissue Tropism in Transgenic Mice", J. of Virol. 66(1); 296-304 (1992).

Resh, Marilyn D., "A myristoyl switch regulates membrane binding of HIV-1 Gag"; Proc. Natl. Acad. Sci., vol. 101(2), 417-418 (Jan. 13, 2004).

Ripoche, Jean et al., "The complete amino acid sequence of human complement factor H", Bichem. J., vol. 249, pp. 593-602 (1988).

Robinson, Jr. W.E., et al., "Antibody-Dependent Enhancement of Human Immunodeficiency Virus Type 1 Infection", The Lancet, pp. 790-794 (Apr. 1988).

Sahu, Arvind, et al., "Specificity of the thioester-containing reactive site of human C3 and its significance to complement activation", Biochem J., vol. 302, pp. 429-436 (1994).

Saphire Andrew C.S., et al., "Host cyclophilin A mediates HIV-1 attachment to target cells via heparans", The EMBO Journal, vol. 18, #23, pp. 6771-6785 (1998).

Sherry, Barbara, et al., "Role of cyclophilin A in the uptake of HIV-1 by macrophages and T lymphocytes"; Proc. Natl. Acad. Sci., vol. 95, pp. 1758-1763 (1988).

Skerka, C., et al., "Mapping of the Complement Regulatory Domains in the Human Factor H-like Protein I and in Factor H" J. of Immun., 155(12); 5663-5670 (Dec. 1993).

Smith, Colleen, Basic Medical Biochemistry: A Clinical Approach, Ch. 17 (2d. ed. 1996).

Spear, G.T., et al., "Human Immunodeficiency virus (HIV)-infected cells and free virus directly activate the classical complement pathway in rabbit, mouse and guinea-pig sera; activation results in virus neutralization by virolysis", J. of Immunology, vol. 73, pp. 377-382 (1991).

Speth, C., et al., "Complement receptors in HIV infection", Immunological Reviews, vol. 159, pp. 49-67 (1997).

Speth, C., et al., "The complement system: Pathophysiology and clinical relevance", The Middle European J. of Medicine, 111/10; 378-391 (1999).

Stahl, Stefan, et al., "Strategies for Gene Fusion", Methods in Molecular Biology, 62: 37-54 (1997).

Stoiber, Herbert et al., "The envelope glycoprotein of HIV-1 gp120 and human complement protein C1q bind to the same peptides derived from three different regions of gp41, the transmembrane glycoprotein of HIV-1, and share antigenic homology", European J. of Immun., vol. 24, pp. 294-300 (1994).

Stoiber, Herbert et al., "Human Complement Proteins C3b, C4b, Factor H and Properdin React with Specific Sites in gp120 and gp41, the Envelope Proteins of HIV-1"; Immunobiology, vol. 193, pp. 98-113 (1995).

Stoiber, Herbert et al., "Efficient Destruction of Human Immunodeficiency virus in Human Serum by Inhibiting the Protective Action of Complement factor H and Decay Accelerating Factor (DAF, CD55)"; J. Exp. Med., vol. 183, pp. 307-310 (Jan. 1996).

Stoiber, Herbert et al., "Role of Complement in HIV Infection"; Annu. Rev. Immunol., 15:649-674 (1997).

Stoiber, Herbert et al., "Role of Complement in the control of HIV dynamics and pathogenis"; Vaccine, 21:S2/77-S2/82 (2003).

Sun, J., Neuraminidase from a Bacterial Source Enhances Both HIV-1 Mediated Syntium formation and the virus Binding/Entry Process; Virol. 2001; Abstract 0340837 A1 (Merck & Co. Inc.); Nov. 8, 1989); p. 4, lines 17-30, p. 5, lines 15-16.

Sun, Jiangfeng et al., "Syncytium Formation and HIV-1 Replication are both Accentuated by Purified Influenza and Virus-associated Neuraminidase", J. of Biol. Chemistry, 277 (12); 9825-9833 (2002).

Tang, Chun et al., "Entropic switch regulates myristate exposure in the HIV-1 matrix protein", Proc. Nat'l Acad. Of Sci., 101(2); 517-522 (Jan. 2004).

Thali, M. et al., "Functional association of cyclophilin A with HIV-1 virions", Nature, 372 (6504): 363-5 (1994).

Thieblemont, N., et al., Triggering of Complement Receptors CR1 (CD35) and CR3 (CD11b/CD18) Induces Nuclear Translocation of NF-KB (p50/p65) in Human Monocytes and Enhances Viral Replication in HIV-infected Monocytic Cells, J. of Immunology, vol. 155, p. 4861-4867 (1995).

U.S. Environmental Protection Agency, Health Assessment Document for Nickel; EPA/600/8-83/012F; National Center for Environmental Assessment, Office of Research and Development, Washington, DC, 1986.

Vajdos, Felix, et al., "Crystal structure of cyclophilin A complexed with a binding size peptide from the HIV-1 capsid p"; Protein Science 6 (11); 2297-2307 (1997).

Vogel, Carl W., "Antibody Conjugates without Inherent Toxicity; The Targeting of Cobra Venom Factor and Other Biological Response Modifiers"; Immunoconuugates, Ch. 9; pp. 170-188 (1987).

Wagner, Edward K., Basic Virology, pp. 105-108, 368 (1999).

Walker, Christopher, et al., "Cationic lipids direct a viral glycoprotein into the Class 1 major histocompatibility complex antigen-presentation pathway", Proc. Natl. Acad. Sci., 89: 7915-1918 (Sep. 1992).

Weiler, John M., et al., "Modulation of the formation of the amplification convertase of complement, C3b,Bb, by native and commercial Heparin"; J. Exp. Med. vol. 147, pp. 409-421 (1978).

Weissenhorn, W., et al., "Atomic structure of the ectodomain from HIV-1 gp41", Nature, vol. 387, pp. 426-630 (May 1997).

Winkelstein, J.A., et al., "Activation of the Alternative Complement Pathway by Pneumococcal Cell Wall Teichoic Acid", J. of Immun., vol. 120, pp. 1678-1178 (1978).

Zipfel, P.F., et al.; "Complement factor H and related proteins: an expanding family of complement-regulatory proteins?" Immunology Today, 15(3): 121-126 (1994).

Azadegan, A.A., et al. 1984, Cobra venom factor abrogates passive humoral resistance to syphilitic infection in hamsters, Infect. Immun. 44(3):740-742.

Flexner, C., et al. 1988 "Characterization of human immunodeficiency virus gag/pol gene products expressed by recombinant vaccinia viruses", Virol. 166(2): 339-349.

Curiel, T.J., "Efficient Foreign Gen Expressin in Epstein-Bar Virus Transformed Human B-Cells", Virol. Feb. 1884, vol. 197, No. 2, pp. 577-585, especially p. 579.

Mata, M. et al., 2001, "Evaluation of a recombinant *Listeria monocytogenes* expressing an HIV protein that projects mice against viral challenge", Vaccine 19:1435-1445.

Kiernan, R. E., et al.: Reversion of a Human Immonodeficiency Virus Type 1 Matrix Mutating Affecting Gag Membrane Binding, Endogenous Reverse Transcriptase Activity, and . . . .

* cited by examiner

IMMUNIZING COMPOSITIONS COMPRISING RECOMBINANT ATTENUATED SELF-REPLICATING VIRAL RNA REPLICONS ENCODING AN EPITOPE OBTAINED FROM THE HIV-1 MATRIX PROTEIN MYRSTATE BINDING SITE

CROSS REFERENCE TO RELATED APPLICATIONS

The present application is a continuing application of application Ser. No. 10/971,229 filed Oct. 22, 2004 now U.S. Pat. No. 7,611,712, which claims priority from U.S. Provisional Application Ser. No. 60/513,827 filed Oct. 23, 2003. All of these related applications are incorporated herein by reference in their entirety.

BACKGROUND OF THE INVENTION

1. Field of the Invention

This invention relates to the field of virology and immunology. Particularly, but not exclusively, it relates to a method of inducing an immune response, and a substance based on the amino terminal end of the matrix protein (p17MA) and covalent binding site for myristate (SEQ ID NOS: 1-3) of the HIV virus for achieving the same.

2. Description of the Related Art

Introduction

Human Immunodeficiency Virus (HIV) is a retrovirus within the slow or Lentivirus group, and is the cause of Acquired Immunodeficiency Syndrome (AIDS). Like many enveloped viruses, HIV fuses the viral and cellular membrane, leading to infection and viral replication. Once it has fused to a host cell, HIV transfers its genome across both the viral and cellular membranes into the host cell.

HIV uses its RNA as a template for making complementary viral DNA in target cells through reverse transcription. Viral DNA can then integrate into the DNA of an infected host. HIV infects cells having surface CD4, such as lymphocytes and macrophages, and destroys CD4 positive helper T lymphocytes. (CD4 represents a Cluster of Differentiation Antigen no. 4 that is part of both Th1 and Th2 cells.) Cell membrane molecules are used to differentiate leukocytes into various effector subsets. In general, four types of cell membrane molecules also known as cluster of differentiation (CD) have been delineated. Type I and II are transmembrane proteins (TPs) with opposite polarity crossing the plasma membrane. Type III TPs crosses the plasma membrane several times and therefore may form pores or channels. Type IV TPs are linked to glycosylphosphatidylinositol (GPI). CD4 is a type I transmembrane protein expressed on a variety of cells including helper/inducer T cells, monocytes, macrophages and antigen presenting cells.

This process relies in part on fusion protein, which is a component of the gp41 glycoprotein. The F protein structure is protease resistant. (Weissenhorn, Nature Vol. 387, pp. 426-430 (1997)) Using X-ray crystallography the three dimensional features of the F protein have been delineated.

The outer membrane proteins, gp41 and gp120, of the HIV virus are non-covalently bound to each other. On the surface of the HIV virion gp120 and gp41 are assembled into a trimeric unit. Three molecules of gp120 are assimilated with three gp41 molecules.

The gp120 molecule binds to a CD4 receptor on the surface of helper T cells as well as macrophages and monocytes. This binding is characterized by a high affinity between the two molecules. High sialic acid content on the surface of the virus reduces the threshold binding energy needed to overcome repulsive electrostatic forces. (Sun, 2002) Membrane fusion of an HIV particle to a target host cell may thus be considered to involve the following steps:

1. interaction of viral bound CypA with host/cellular heparin.
2. viral attachment to target cell via CypA/heparin interaction.
3. gp120 binding to the CD4 molecule of the target cell. This process requires coreceptor proteins also known as chemokine receptors (CCR5 for T cells and CXCR4 for macrophages). The virus then begins to fuse with the cell, producing structural or conformational changes and exposing other receptors;
4. conformational three dimensional and/or tertiary structure changes of the gp120 molecule exposing the fusion domain or F protein of gp41;
5. dissociation of the gp120 from the gp41 molecule as a result of the conformational change and the shedding of gp120;
6. folding of gp41 upon itself before piercing the plasma membrane of the target cell
7. unfolding of the F protein; and
8. fusion of the membranes of the viral particle and host cell.

The insertion of the fusion peptide disrupts the integrity of the lipids within the targeted host cell membrane. F protein links the viral and the cellular membranes, such that upon unfolding of the fusion protein, the plasma membrane of the target cell and the viral membrane are spliced together.

The viral membrane of HIV is formed from the plasma membrane of an infected host cell when the virus buds through the cell's membrane. Thus, the envelope includes some of the lipid and protein constituents of the host cell. (Stoiber, 1996) (Stoiber, 1997) Some enveloped viruses use spike proteins, etc., to mimic the host molecules in order to bind to target cell receptors and to enter other target cells. However, these spikes can also be antigenic surfaces for immune system recognition and viral destruction. HIV protects itself against immune challenge (humoral and CD8 mediated) by the host. In addition to the variability of conformational changes, gp120 provides other surface features that disguise it from immune detection and attack, such as a coating of glycoproteins, covalently bound sialic acid residues, or steric occlusion. (Haurum, 1993) In short, HIV activates a variety of immune responses to its own advantage.

The core of the HIV virion functions as a command center. Inside an HIV virion is a capsid composed of the viral protein p24 (CA). The capsid also holds two single strands of RNA, each strand of which provides a copy of HIV's nine genes, which encode 15 proteins. Of the nine genes, three (gag, pol and env) are considered essential. Six additional genes are also found within the 9-kilobase pair RNA genome (vif, vpu, vpr, tat, rev, and nef). More specifically, the env gene holds the information or code for creation of gp160, which breaks down into gp120 and gp41. Likewise the gag gene encodes the matrix (p17 or MA), capsid (p24 or CA), nucleocapsid (p9, p6 or NC). The pol gene provides the genetic information for the virus to produce the reverse transcriptase enzyme as well as the integrase enzyme and RNAseH enzyme. The other six genes are regulatory, and control the mechanisms of infection and replication (tat, rev, nef, vif, vpr and vpu). Among other things, the nef gene holds information for efficient replication, while vpu holds information regulating the release of new viral particles from the infected host cell.

Ultimately, in order for HIV to infect a target cell, it must inject the HIV genetic material into the target cells cytoplasm.

As noted above, the nef gene is believed to aid efficient replication of HIV. The creation of a new virus particle occurs at the host cell's membrane. Nef appears to affect an infected cell's environment in a way that optimizes replication. Viral proteins collect near the host cell's membrane, bud out within the membrane, and break away. These proteins are the three structural proteins (gp160, gp120, gp41) plus two other internal precursor polyproteins (Gag and the Gag-Pol). The Gag-Pol protein brings two strands of the positive RNA into the bud, while protease cuts itself free. After the virus has budded, protease cuts itself free and cuts up the rest of the proteins in Gag or Gag-Pol, releasing the various structural proteins and reverse transcriptase. The viral proteins are not functional until they are separated by the protease. Thus, protease is responsible for cleavage of Gag-Pol and the smaller Gag polyprotein into structural proteins. Released proteins p24, p7 and p6 form a new capsid, while at the base of the lipid membrane is p17. In this process, gp160 breaks down into gp120 and gp41 by a host enzyme.

The gag gene gives rise to a 55-kilodalton (kD) Gag precursor protein, also called p55 ($Pr55^{gag}$), which is expressed from the unspliced viral messenger RNA (mRNA). During translation, the N terminus of the p55 is myristylated, triggering its association with the cytoplasmic aspect of cell membranes. The membrane-associated Gag polyprotein recruits two copies of the viral genomic RNA along with other viral and cellular proteins that trigger the budding of the viral particles from the surface of an infected cell. After budding, p55 is cleaved by the virally encoded protease (a product of the Pol gene), during the process of viral maturation into four smaller proteins designated MA (matrix or p17), CA (capsid or p24) and NC (nucleocapsid or p9 and p6.) (Cohen, P. T., et al., The AIDS Knowledge Base, 149 (1999)) Thus, the HIV core contains four proteins, including p17. In summation, the HIV virus is encoded by three large genes encoding structural and enzymatic peptides (gag, pol and env) and six smaller regulatory genes (vif, vpu, vpr, tat, rev and nef). (Sande, Merle A., et al., The Medical Management of AIDS, Ch. 2 (6th ed. 1999))

$Pr55^{gag}$ (the polypeptide encoded by the gag gene) is cleaved by viral protease to generate four large and two small peptides. From N to C terminus the following proteins are proteolytically produced: matrix (p17MA), capsid (p24CA), nucleocapsid (p7NC), and p6. The two small peptides include p2 located between p24CA and P7NC and p1 located between p7NC and p6. The matrix protein assembles inside the viral lipid bilayer and stabilizes it. (Zhou, Wenjun, et al., J. of Virology, pp 8540-8548 (December 1996))

Two critical steps in HIV viral replication are controlled by the matrix protein and the larger polyprotein precursor $Pr55^{gag}$. (1) The nuclear targeting signal of the matrix protein. (2) The strong localizing signal to the cell plasma membrane of $Pr55^{gag}$ (Lee, Young-Min, et al., J. of Virology, pp 9061-9068 (November 1998))

The $Pr55^{gag}$ localizing signal can differentiate between the membranes encompassing cellular organelles and the plasma membrane. The key to the specificity of plasma membrane binding is conferred by a combination of a basic residue rich domain (amino acids 17-31) and the presence of an N-terminal myristoyl moiety. The 14 carbon fatty acid myristate is cotranslationally attached to the N-terminus of the HIV $Pr55^{gag}$. This plasma membrane targeting of $Pr55^{gag}$ is essential for viral assembly and budding. (Zhou, 1996)

The active nuclear transport of the preintegration complex of HIV disease is controlled by two viral proteins, p17MA and Vpr. After fusion of the viral membrane to the target cell membrane the matrix protein becomes detached from the inner aspect of the lipid bilayer and several matrix molecules with viral RNA cross the nuclear membrane and enter the nucleoplasm. Therefore HIV-1 can infect non-dividing cells and is not dependent on the disintegration of the nuclear envelope which occurs during mitosis. Most viruses are not capable of infecting non-dividing cells. (Zhou, 1996)

The differential membrane binding of $Pr55^{gag}$ and MA is due to a myristoyl switch. Myristate is covalently bound to the N-terminal glycine amino acid of the MA protein. (Ono, Akira, et al., J. of Virology," pp 4136-4144 (May 1999)) Upon cleavage of the $Pr55^{gag}$ by viral protease the myristate moiety inserts into a preexisting cavity of the MA molecule. This change in the three dimensional structure of the MA molecule occurs as a result of altered conformation in amino acids 9-11 (serine, glycine, glycine) Therefore the MA molecule has less electrostatic force holding it to the lipid bilayer than its larger precursor $Pr55^{gag}$. Disruption of the viral plasma membrane upon fusion to a target cell destabilizes the matrix complex allowing for nuclear localization to occur. The flipping of the myristate moiety in and out of a protected cleft is known as the myristoyl switch and is found in other proteins including ADP ribosylation factor (ARF), recoverin and c-Abl. Current estimates of myristoylated proteins in the human genome approximate 0.5%. (Resh, Marilyn D., "A myristoyl switch regulates membrane binding of HIV-1 Gag," Proc. Natl. Acad. Sci., Vol 101 (2) 417-418 (Jan. 13, 2004))

Myristylated proteins are covalently attached to myristic acid [tetradecanoic acid $CH_3 (CH_2)_{12} COOH$]. Myristic acid is a carboxylic acid. Carboxylic acid molecules are polar and like alcohol molecules can form hydrogen bonds with each other and with other kinds of molecules. Myristic acid is virtually insoluble in water but is highly soluble in lipids explaining in part the plasma membrane localizing signal inherent in the MA molecule.

Fatty acid components of proteins can serve as regulated targeting devices. (Tedeschi, Henry, Cell Physiology Molecular Dynamics, ch. 4 (2003)) The carboxyl end of several myristylated proteins provide hydrophobic anchors used in protein targeting and in signal transduction. The fatty acid site may attach via hydrophobic interactions to the phospholipid bilayer. Myristic acid is added cotranslationally (while the protein is being synthesized) on terminal glycine amino acids.

The MA polypeptide (p17) is derived from the N-terminal, myristylated end of p55. Most MA molecules remain attached to the inner surface of the virion lipid bilayer, stabilizing the particle. A subset of MA is recruited inside the deeper layers of the virion where it becomes part of the complex which escorts the viral DNA to the nucleus after fusion of the viral and host membranes have occurred. These MA molecules facilitate nuclear transport of the viral genome because a karyophilic signal on MA is recognized by the cellular nuclear import machinery. This is important because this allows HIV to infect non-dividing cells, such as macrophages, which is an unusual property for a retrovirus. (Cohen, P. T., et al., The AIDS Knowledge Base 149 (1999))

Most HIV vaccines, however, use portions of envelope glycoproteins (gp160, gp120, and gp41) in an attempt to induce production of neutralizing antibodies against the envelope spikes of the virus. (Johnston, et al., 2001) Some have been successful in producing high titers of neutralizing antibodies. The thought behind this approach is that the antibodies that bind to these glycoproteins would neutralize the virus and prevent infection. A functioning immune system could then activate the complement system, which would cascade to lysis and destroy the virus. The complement system is a series of circulating proteins that "complements" the role of antibodies. The components of the complement system are activated in sequence or turn, which is the complement cascade. The conclusion of complement is a protein complex, the Membrane Attack Complex (MAC) that seeks to attach to an invading organism's surface and to destroy it by puncturing its cell membrane.

Immune Response

Thus, a primary effect of HIV is to deplete the CD4 T+ cells, which lowers overall immune activity. As described above, HIV infection centers on CD4 T+ cells, but it also infects B cells, blood platelets, endothelial cells, epithelial cells, macrophages, etc. As CD4 T+ cells are depleted, the B cell response becomes deregulated. Hypergammaglobulinemia with ineffective antibodies characterizes HIV progression. Further, cytotoxic CD8 T cells are rendered incompetent and are unable to recognize and attack viral infection. This is due in part to transfection of uninfected CD8 cells with the tat protein manufactured in infected CD4 cells.

The CD4 T+helper (Th) cells produce cytokines and can be grouped into either Th1 cells or Th2 cells. The Th1 cells promote cell-mediated immunity while Th2 cells induce humoral immunity. The cytokines are chemical messengers or protein attractants that regulate immunologic responses. The depletion of CD4+ helper cells in HIV disease results in reduced synthesis of certain cytokines and enhanced synthesis of others. Cytokine disregulation depresses the activity of the natural killer cells and macrophages. Further, the loss of interleukin-2 slows the clonal expansion and activation of mature T cells.

Different viral traits augment or diminish cell mediated and humoral response. In some strains and phases of progression, HIV may be characterized as a failure of Th1 response, accompanied by overactive but ineffective Th2 response. The balance between Th1 and Th2 immune response appears to depend in part on the HIV strain(s) and in part on the genetic milieu of the infected animal. For example, long term non-progressors mount an effective Th1 response to HIV disease. (Pantaleo, 1995)

An immunogenic compound directed to creating a balanced immune response and strengthening or reinforcing the type of immune response suppressed by a particular virus would be of value. (Hogan, 2001)

Cellular Response

HIV appears to trigger an initially strong cellular immune response that is not maintained over time and ultimately fails to control the infection. (McMichael, 2001)

CD8 cytotoxic T-cells (Tc) recognize a cell presenting a foreign antigen by MHC (Major Histocompatibility Complex) class 1 molecules on the surface, and attack it. CD4 helper cells (Th) stimulate macrophages that have ingested a viral microbe to kill the microbe. The cytokines or interleukins produced by the CD4 cells determine in part whether the immunologic response to a pathogen is primarily TH1 or TH2 driven. In some infections CD4 cells produce interleukin-4 and interleukin-5, which select for B-cells. B cells present antigen complexed with MHC class II molecules. In other infections CD4 cells produce IL-2 which select for cytotoxic T cells. This division or restriction of functions in recognizing antigens is sometimes referred to as MHC restriction. MHC class I generally presents endogenously synthesized antigens, such as viral proteins, while MHC class II generally presents extracellular microorganisms or antigens such as bacterial or viral proteins which have been phagocytosed by antigen presenting cells. The antigen presenting cells then bind the antigen with MHCII protein on its surface. The CD4 cell interacts with this antigen through its T cell receptor and becomes activated. This contributes to the ineffectiveness of inactivated vaccines to produce Tc cytotoxic response. (Levinson, 2002)

As noted above, T cells mediate cellular response. The antigen presenting cells, along with MHC molecules (or Human Leukocyte Antigen—HLA) present peptide portions of HIV antigens (or epitopes) to their respective T cells, triggering T cell response. The type of epitope presented to a T cell depends on the type of HLA molecule (e.g., HLA A, B, C, DR, DQ, DP) and the amino acid in the peptides. Genetic limitations in HLA molecules or mutant epitopes may lead to epitope escape and HIV persistence. (McMichael, 2001) As noted above, Th cells produce cytokines for general (i.e., Th 1 and Th2) immune response, but in the case of HIV this is suppressed by infection of the Th cells. HIV specific Th cells that respond to HIV antigens are eventually infected and destroyed or suppressed. This leads to a secondary effect on cytotoxic T cells. Cytotoxic T cells demonstrate a variety of antiviral activities (such as the production of performs, granzymes, FasL and cytokines), after recognizing and attacking foreign antigens on infected cells that are bound by MHC class I molecules. HIV can reduce the expression of HLA class I molecules in infected cells, reducing the ability of cytotoxic T cells to recognize and attack the infected Th cells. Further, the infection and depletion of Th cells disrupt the ability of cytotoxic T cells to mature and to address mutant virions. (McMichael, 2001) Typically, in a viral infection the cytotoxic T cells eliminate or suppress the virus. But HIV counters cellular immune response by infecting immune cells and impairing the response of Th cells and cytotoxic T cells.

Thus, an immunogenic compound that stimulated Th1 activity would promote favorable immune response against HIV.

Humoral Response

The humoral arm of the immune system consists of B cells that, upon stimulation, differentiate into antibody producing plasma cells. The first antibodies to appear are IgM, followed by IgG in blood, or IgA in secretory tissues. A major function of these antibodies is to protect against infectious disease and their toxins. Antibodies not only neutralize viruses and toxins, but also opsonize microorganisms. Opsonization is a process by which antibodies make viruses or bacteria more easily ingested and destroyed by phagocytic cells. Phagocytic cells include both polymorphonuclear neutrophils (PMNs) and tissue macrophages. PMNs comprise about 60% of the leukocytes in the blood of an uninfected patient. The number of PMNs and tissue macrophages may increase or decrease with certain infectious disorders. For example, typhoid fever is characterized by a decrease in the number of leukocytes (i.e., leukopenia). Both PMNs and macrophages phagocytose consume bacteria and viruses. PMNs do not present antigen to helper T cells, whereas macrophages and dendritic cells do.

Phagocytosis includes (1) migration, (2) ingestion, and (3) killing. Tissue cells in the infected area produce small polypeptides known as chemokines. The chemokines attract PMNs and macrophages to the site of an infection. Then the bacteria are ingested by the invagination of the PMN cell membrane around the bacteria to form a vacuole or phagosome. This engulfment or opsonization is enhanced by the binding of IgG antibodies (opsonins) to the surface of the bacteria. The C3b component of the complement system enhances opsonization. (Hoffman, R. Hematology Basic Principles and Practice Ch. 37 (3rd ed. 2000)) The cell membranes of PMNs and macrophage have receptors for C3b and the Fc portion of IgG.

With engulfment, a metabolic pathway known as the respiratory burst is triggered. As a result two microbicidal agents, the superoxide radical and hydrogen peroxide are produced within the phagosomes. These highly reactive compounds often called reactive oxygen intermediates are synthesized by the following chemical reactions:

$$O_2 + e^- \rightarrow O_2{-}$$

$$2O_2{-} + 2H^+ \rightarrow H_2O_2 \text{ (Hydrogen peroxide)} + O_2$$

The first reaction reduces molecular oxygen to form the superoxide radical, which is a weak microbicide. The second reaction, which is catalyzed by the enzyme superoxide dismutase within the phagosome, produces hydrogen peroxide. In general, hydrogen peroxide is a more effective microbicide than the superoxide radical. The respiratory burst also produces nitrous oxide (NO), another microbicide. NO contains a free radical that participates in the oxidative killing of ingested viruses and bacteria phagocytosed by neutrophils and macrophages. The NO synthesis within the phagosome is catalyzed by the enzyme NO Synthase, which is induced by the process of phagocytosis.

The killing of the organism within the phagosome is a two step process that consists of degranulation followed by the production of hypochlorite ions, which is the most effective of the microbicidal agents. Two types of granules are found within the cytoplasm of the neutrophils or macrophages. These granules fuse with the phagosome to form a phagolysosome. The contents of the granules are then emptied. These granules are lysosomes that contain a variety of enzymes essential to the killing and degradation. Two types of lysosomal granules, which are differentiated by their size, have been identified. The larger lysosomal granule, which constitutes about 15% of the total, contains several enzymes including myeloperoxidase, lysozyme, and other degradative enzymes. The remaining 85% are smaller granules, which contain lactoferrin and other degradative enzymes, such as proteases, nucleases, and lipases. The actual killing or destruction of microorganisms occurs by variety of mechanisms, some oxygen-dependent and some oxygen-independent. The most important oxygen-dependent mechanism is the production of the hypochlorite ion catalyzed by myeloperoxidase:

$$Cl^- + H_2O_2 \rightarrow ClO^- + H_2O$$

Antibodies are glycoproteins, composed of light (L) and heavy (H) polypeptide chains. The simplest antibody has a "Y" shape and consists of four polypeptides: 2H-chains and 2 L-chains. Disulfide bonds link the four chains. An individual antibody molecule will have identical H- and identical L-chains. L- and H-chains are subdivided into two regions: variable and constant. The regions have segments or domains, which are three-dimensionally folded and repeating. An L-chain consists of one variable (V1) and one constant (C1) domain. Most H chains consist of one variable (VH) and three constant (CH) domains. The variable regions are responsible for antigen (virus, bacteria, or toxin) binding. The constant regions encode several necessary biologic functions including complement fixation and binding to cell surface receptors. The complement binding site is located in the CH2 domain.

The variable regions of both L- and H-chains have three highly variable (or hypervariable) amino acids sequences at the amino-terminal portion that makes up the antigen binding site. Only 5-10 amino acids in each hypervariable region form this site. Antigen-antibody binding involves electrostatic forces and van der Waals' forces. In addition, hydrogen and hydrophobic bonds are formed between the antigen and hyper-variable regions of the antibody. The specificity or "uniqueness" of each antibody is in the hyper-variable region; the hyper-variable region is the thumbprint of the antibody.

The amino-terminal portion of each L-chain participates in antigen binding. The carboxy-terminal portion contributes to the Fc fragment. The Fc fragment (produced by proteolytic cleavage of the hinge region of the antibody molecule separating the antigen binding sites from the rest of the molecule or the Fc fragment) expresses the biologic activities of the constant region, specifically complement fixation. The H-chains are distinct for each of the five immunoglobulin classes. The heavy chains of IgG, IgA, IgM, IgE and IgD are designated γ, α, μ, ε and δ respectively. The IgG immunoglobulin class opsonizes microorganisms; thus, this class of Ig (immunoglobulin) enhances phagocytosis. (Hoffman, Ronald, et al., Hematology Basic Principles & Practice, ch. 36 & 39 (3rd ed. 2000))(Levinson, Warren, Medical Microbiology & Immunology, Ch. 59 & 63 (7th ed. 2002)) Receptors for the γ H-chain of IgG are found on the surface of PMNs and macrophages. IgM does not opsonize microorganisms directly because there are no receptors on the phagocyte surface for the μH-chain. IgM does, however, activate complement, and the C3b protein can opsonize because there are binding sites for C3b on the surface of phagocytes. (Levinson, 2002) IgG and IgM, are able to initiate complement cascade. In fact, a single molecule of IgM can activate complement. Activation of complement by IgG requires two cross-linked IgG molecules (IgG1, IgG2, or IgG3 subclasses, IgG4 has no complement activity). A variety of non-immunologic molecules, such as bacterial endotoxin, can also activate the complement system directly.

The complement system consists of approximately twenty proteins that are normally in serum. The term "complement" indicates how these proteins complement or augment other components in the immune system, such as antibodies and immunoglobulin. Complement cascade has three important immune effects: (1) lysis of microorganisms; (2) generation of mediators that participate in inflammation and attract PMNs; and (3) opsonization.

Complement cascade occurs via one of three paths: (1) classic; (2) lectin; and (3) alternative. (Prodinger, Wm., et. al., Fundamental Immunology, Ch. 29 (1998)) These pathways are diagrammed in FIG. 1. The dashed line shows that proteolytic cleavage of the molecule at the tip of the arrow has occurred. A line over a complex indicates that it is enzymatically active. Although the large fragment of C2 is sometimes interchangeably labeled C2a or C2b, for convention, here small fragments are designated as "a," and all large fragments as "b." Hence, the C3 convertase is C4b,2b. Note that proteases associated with the mannose-binding lectin cleave C4 as well as C2. Each of these pathways leads to the creation of the Membrane Attack Complex (MAC).

With the antibody attached to a specific component of a virus or bacteria, the MAC is able to perforate the microorganism's protective cover and allow blood plasma and electrolytes to enter the microorganism, and at the same time provide a means for egress of the microorganism's internal structural components.

In the classic pathway, antigen-antibody complexes activate C1 to form a protease, which cleaves C2 and C4 to form a C4b,2b complex. C1 is composed of three proteins: C1q, C1r, and C1s. C1q is composed of 18 polypeptides that bind to the Fc portion of IgG and IgM. Fc is multivalent and can cross-link several immunoglobulin molecules. C1s is a proenzyme that is cleaved to form an active protease. Calcium is required as a cofactor in the activation of C1. Further, activation of C1 requires multi-point attachment of at least two globular heads of C1q to the Fc domains of IgG and/or IgM. The changes induced in C1q on binding multiple Fc immunoglobulins is transmitted to the C1rs subunits, resulting in proteolytic autoactivation of the C1r dimer, which then proteolytically activates or cleaves C1s. As seen above, activated C1s possesses the catalytic site for proteolytic splicing of C4 and C2. An enzyme complex, C4b,2b, is produced. This functions as a C3 convertase, which cleaves C3 molecules into two fragments, C3a and C3b. C3b forms a complex with C4b and C2b, producing a new enzyme, (C4b,2b,3b) which is a C5 convertase.

In the lectin pathway, mannan-binding lectin (MBL, or mannose-binding protein) binds to the surface of microbes expressing mannan. MBP is a C-type lectin in plasma that has a structure similar to that of C1q, and binds to C1q receptors enhancing phagocytosis. Mannose is an aldohexose found on the surface of a variety of microorganisms. The first component of the lectin pathway is designated mannose (or mannan) binding protein (MBP). A C-terminal carbohydrate recognition domain has affinity for N-acetylglucosamine and confers the capacity for MBP to directly opsonize microorganisms expressing mannose-rich surface coats. In the blood, MBP circulates as a stable complex with a C1r-like proenzyme and a C1s-like proenzyme (designated MBP-associated serine protease, or MASP-1 and MASP-2 respectively). The MBP-MASP-1, MASP-2 complex binds to the appropriate carbohydrate surface. This results in conformational change in the MBP protein which leads to auto-activation of MASP-1 by internal peptide cleavage converting MASP-1 to an active serine protease. Like C1r, active MASP-1 cleaves MASP-2 activating it. Active MASP-2 exhibits the capacity to proteolytically activate both C4 and C2 to initiate assembly of the C4b,2b (C3 convertase) enzyme complex. As with the classic pathway, this leads to the production of C5 convertase.

In the alternative pathway many unrelated cell surface structures, such as bacterial lipopolysaccharides (endotoxin), fungal cell walls, and viral envelopes, can initiate the process by binding to C3($H_2O$) and factor B. This complex is cleaved by a protease, factor D, to produce C3b,Bb, which acts as a C3 convertase to generate more C3b. In contrast to the sequential enzyme cascade of the classical pathway, the alternative pathway uses positive feedback; the principal activation product, C3b, acts as a cofactor for C3b,Bb, which is also responsible for its own production. Thus, the alternative pathway is continuously primed for explosive C3 activation. The rate of C3 activation is governed by the stability of the C3b,Bb enzyme complex. Proteolysis of factor B by factor D produces a small fragment (Ba) and a large fragment (Bb). The larger Bb fragment combines with either C3($H_2O$) or C3b. Through a catalytic site in Bb, the complex C3($H_2O$),Bb can proteolytically convert C3 to C3a and C3b. Nascent C3b generated by this mechanism is capable of binding additional factor B. Therefore the alternative complement pathway has at least two positive feedback loops enhancing the production of C3b. As shown in FIG. 1, this route also leads to the production of C5 convertase.

For each pathway the C5 convertase (C4b,2b,3b or C3b, Bb, C3b) cleaves C5 into C5a and C5b. C5b binds to C6 and C7, to form a complex that interacts with C8 and C9, ultimately producing MAC (C5b,6,7,8,9). (Hoffman, 2000)

Regardless of which complement pathway is activated, the C3b complex is a central molecule for complement cascade. Immunologically C3b fulfills three roles:

1. sequential combination with other complement components to generate C5 convertase, the enzyme that leads to production of MAC (C5b,6,7,8,9);
2. opsonization of microorganisms. Phagocytes have receptors for C3b on their cell surface.
3. binding to its receptors on the surface of activated B cells, which greatly enhances antibody production. (Parham, Peter, The Immune System, ch. 7 (2nd ed. 2004))

The humoral response includes certain regulators of this system, such as Complement Factor H, that are vulnerable to exploitation by HIV. Any microorganism with the capacity to limit the activity of complement cascade could theoretically protect itself against the humoral arm of the immune system. (Stoiber, Heribert, Role of Complement in the control of HIV dynamics and pathogenis, Vaccine 21: S2/77-S2/82 (2003)) Thus, the complement cascade is an Achilles heel of the humoral arm.

HIV Interaction with Humoral Response

Retroviruses can activate the complement system in the absence of antibodies. (Haurum, J., AIDS, Vol. 7(10), pp. 1307-13 (1993)) Complement activation by HIV envelope glycoproteins has been found to be mediated by the binding of MBP to carbohydrates on natural envelope protein produced in virus-infected cells, as well as on glycosylated recombinant envelope proteins. (Haurum, John, AIDS, Vol. 7(10), pp. 1307-13 (1993)) (Speth, C., Immunology Reviews, Vol. 157, pp. 49-67 (1997)) Activation of the classical complement pathway and lectin pathway by retrovirus envelopes can be initiated by the binding of MBP to carbohydrate side chains of envelope glycoproteins. The transmembrane protein of HIV-1, gp41, has been shown to be non-covalently associated with gp120. Complement component, C1q, also binds to gp41. In the cell-external part (ectodomain) of gp41, three sites (aa 526-538; aa 601-613 and aa 625-655) bind both gp120 and C1q. Thus, C1q and gp120 are both structurally and functionally homologous. The interaction between gp41 and C1q is calcium dependent unlike the association of gp41 and gp120 which is calcium independent.

HIV triggers the classical and lectin pathway in an antibody-independent manner which leads to the infection of complement receptor-positive cells by HIV. The binding of C1q to gp41 may facilitate infection in different ways. C1q binds directly to HIV-infected cells that are also infected with HIV-1. C1q retains its ability to bind to the C1q receptor, also known as the collectin receptor. Further, gp41 interacts directly with C1q anchored on the plasma membrane of macrophages. In both cases, HIV has the opportunity for C1q-mediated CD4 independent contact with cells.

The homology of gp120 and C1q raises the possibility that gp120 may interact directly with the C1q receptor, and thereby facilitate the entry of HIV into macrophages in a CD4-independent manner. (Stoiber, Heribert, European Journal of Immunology, Vol 24, pp. 294-300 (1994)) Antibodies to gp120 are able to cross react with C1q and may be responsible, at least in part, for the significantly low C1q concentration in HIV-1 patients. C1q is one of the factors responsible for the clearance of insoluble immune complexes, and its absence might contribute to the significantly high concentrations of insoluble immune complexes noted in individuals infected with HIV. (Procaccia, S., AIDS Vol 5, p. 1441 (1991)) Hypocomplementemia which characterizes HIV disease is correlated with HIV associated opportunistic infections and viral associated malignancies.

Regulators of complement activity can be found attached to plasma membranes. Others circulate freely in human plasma and lymph. Many regulators of complement activity (RCA) have been characterized and virtually every step in all three pathways is subject to positive and negative controls. Three enzymatic complexes (C3 convertases, C5 convertases, MAC complex) are focal within the complement cascade and are subjected to multiple inhibitors or catalysts.

Several proteins that control the complement activation pathways circulate in plasma as freely soluble molecules, and can either control C3 activation in the fluid phase or inhibit formation of MAC on cell surfaces. Regulators of complement, such as Factor H and low-molecular-weight Factor H-like proteins, have been shown to mediate this function. Factor H interacts with gp120, enhancing syncytium formation and soluble CD4 (sCD4) induced dissociation of the envelope glycoprotein (env) complex. Factor H only binds activated gp120 after it has engaged CD4, suggesting that the binding site is hidden within the env complex, and becomes exposed only after interaction of gp120 with CD4. (Pinter, C., AIDS Research in Human Retroviruses, Vol. 11, (1995)) The gp120 molecule binds to the CD4 receptor on helper T cells. The virus then fuses with the T cell. The fusion domain is located on gp41. Upon fusion, the gp120 fragment is shed. The gp41 ectodomain becomes exposed after shedding gp120. Binding sites for C1q and factor H on gp41 become unmasked.

HIV activates human complement systems even in the absence of specific antibodies. (Stoiber, H, J. Ann. Rev. Immunology, Vol. 15, 649-674 (1997)) This would result in viral inactivation if complement were unimpeded. The complement process if unimpeded would produce membrane attack complex (MAC), triggering virolysis. However, HIV avoids virolysis by incorporating into its structure various molecules of the host (e.g., DAF/CD55) that regulate complement. HIV includes these molecules in the virus membrane upon budding from infected cells, or by attachment to the gp41 and gp120 structures. (Stoiber, H., J. Ann. Rev. Immunology, Vol. 15, 649-674 (1997)) This interaction with complement components enables HIV to take advantage of complement components to enhance infectivity, follicular localization, and broaden its target cell range. At the same time, HIV defends against the humoral arm.

Proteins such as Factor H and CR1 have both cofactor and decay accelerating activities on the C3 convertases. (Stoiber, H, J. Ann. Rev. Immunology, Vol. 15, 649-674 (1997)) C3b integrity is essential for the complement cascade to culminate in cell lysis. C3b is rapidly cleaved by a serine protease (complement Factor 1-CF1) after interaction with appropriate complement receptors. Proteins that mediate this reaction possess cofactor activity for CF1. Some proteins down regulate complement activation by inhibiting the assembly and/or by favoring the dissociation of C3b and C4b generating enzymes (convertases). This activity is termed decay acceleration and is characteristic of the CD55 (DAF) protein molecule.

Serum lacking Factor H will lyse HIV and infected cells, but not cells that are uninfected. (Stoiber, H., J. Exp. Med., 183:307-310 (1996)) In the presence of Factor H, lysis of HIV has been shown to occur when the binding of Factor H was inhibited by a monoclonal antibody directed to a Factor H binding site in gp41. Human serum that is devoid of Factor H effectively lyses HIV virions. But to date, there has been no indication of how to implement this growing knowledge of the relationship of HIV and Factor H to the human complement.

RELATED ART

Despite profound efforts, there is no curative vaccine for HIV. Various steps of the HIV life cycle have been targeted by inventors. To date, research has not found a composition that would foster an effective immune response against the immunosuppressive retrovirus HIV-1. Most HIV vaccines use portions of the envelopes of surface glycoproteins (gp160, gp120, and gp41) of the virus in an attempt to induce production of neutralizing antibodies against the envelope spikes of the virus. (Johnston et al., 2001) Some have been successful in producing high titers of neutralizing antibodies. The thought behind this approach is that the antibodies that bind to these glycoproteins would neutralize the virus and prevent infection. A functioning immune system could then activate the complement system, which would cascade to lysis and destroy the virus. However, the impairment of humoral response described above limits the effectiveness of these vaccines. A number of drugs or compositions (AZT, ddI, ddC, d4T and 3TC) inhibit reverse transcription. These 2',3'-dideoxynucleoside analogs can be effective against certain strains, but are vulnerable to the genomic mutability of HIV. (Deeks, Steven, The Medical Management of Aids, Ch. 6 (6th ed. 1999)) These medications also face problems of toxicity, cost, complex treatment regimens, drug-drug interactions, as well as drug resistance.

Interfering with other aspects of the HIV life cycle is less common. Some efforts have targeted interactions between HIV $Pr55^{gag}$ and the cellular membrane. A few efforts, such as U.S. Pat. No. 6,627,197 to Keener et al., employ the N terminus of the Pr55 protein (which attaches to myristic acid) as a target molecule for protease activated ricin in order to kill infected cells. However, there remains a need for immunogenic compositions and methods that employ the amino terminal end of the matrix protein (p17MA) and covalent binding site for myristate on the HIV virus while stimulating individual elements of both the cellular and humoral immune responses.

SUMMARY OF THE INVENTION

As described above, HIV is capable of infecting both dividing and non-dividing cells, such as macrophages. Thus, in addition to impairing immune response by attacking or binding complement regulators, HIV impairs cellular portions of the immune system. Myristate binds to the matrix protein, triggering association with the cytoplasm of cell membranes. Accordingly, the present invention is an immunogenic composition based on the covalent binding site for myristate on the HIV matrix protein, including the amino terminal end of the matrix protein (p17MA), and a method for preparing and using the same. The present invention contemplates three categories of embodiments: protein or protein fragments (SEQ ID NO: 1), messenger RNA (SEQ ID NO: 3), or DNA/RNA (SEQ ID NOS: 2-3). DNA/RNA compositions may be either naked or recombinant. The present invention further contemplates use with a variety of immune stimulants.

BRIEF DESCRIPTION OF THE DRAWINGS

FIG. 1 shows is a depiction of the human complement cascade pathways.

FIG. 2 depicts the categories of embodiments for amino terminal end of the matrix protein (p17MA) and the covalent binding site for myristate on the HIV virus within the present immunogenic composition.

Figure 7:
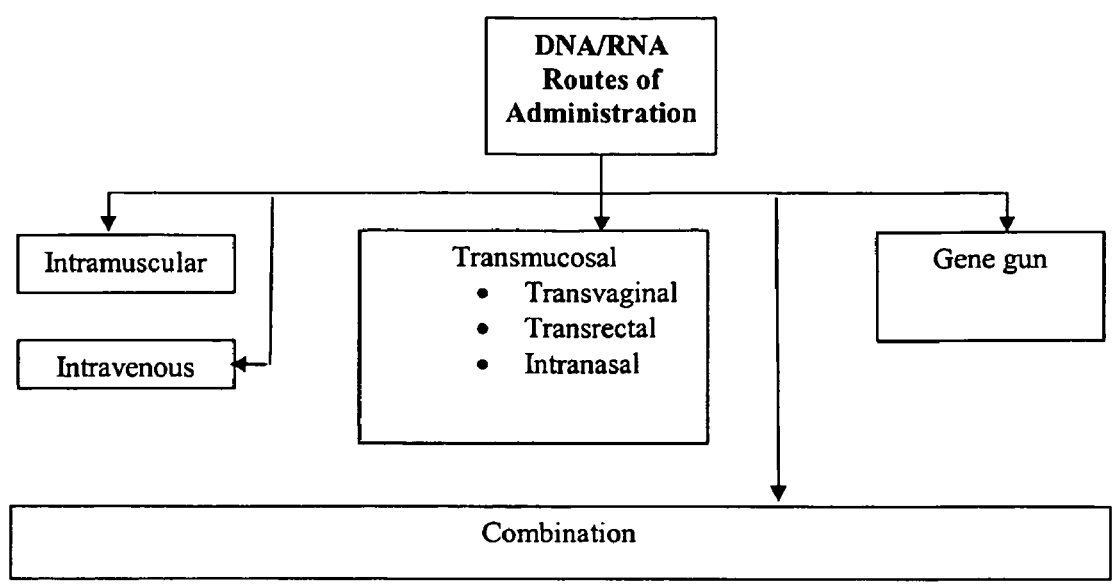

FIG. 7 describes customary routes of administration for DNA.

Figure 8:
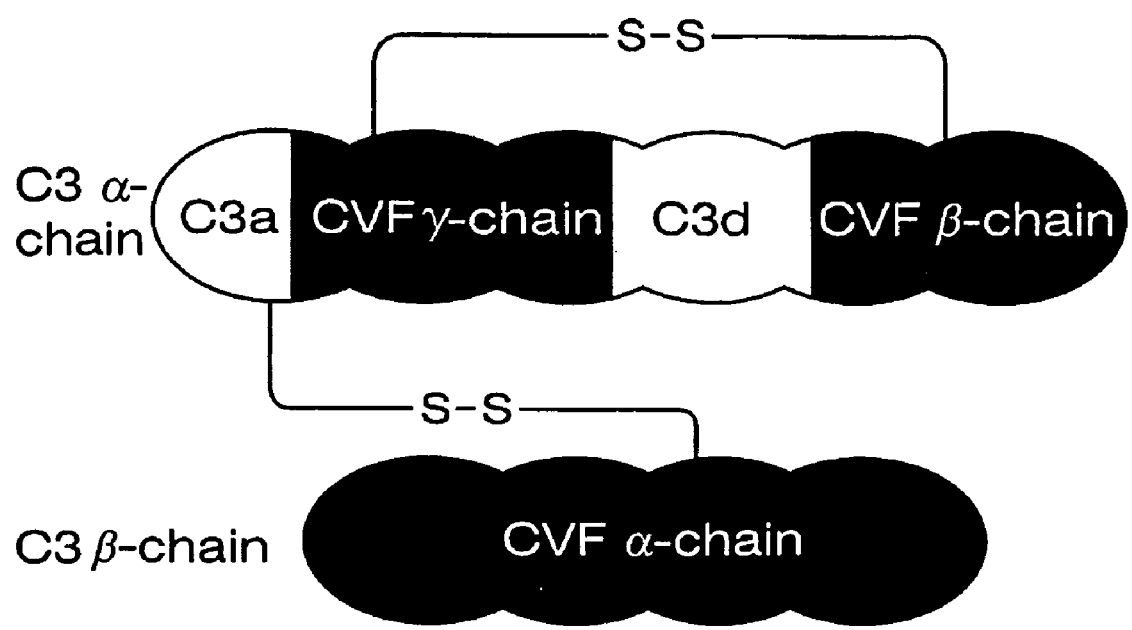

FIG. 8 is a schematic drawing showing the chain structures of C3 and CVF and their relationship.

DESCRIPTION OF THE INVENTION

A. Introduction

The present invention is an immunogenic composition based on the covalent binding site (SEQ ID NO: 1) for myristate on the HIV matrix protein, including the amino terminal end of the matrix protein (p17MA). Both the mature and immature form of the matrix protein may be used. Further, the genetic sequence encoding the protein (SEQ ID NOS: 2-3) may also be used to produce a recombinant embodiment.

In addition to the immune functions described above, another function of the immune system is the creation of a "memory" of an antigen. A later exposure to the same antigen might then prompt a more effective early response. This memory is created by antigen specific lymphocytes. Thus, memory lymphocytes, along with other cells and factors, provide both immediate protection in peripheral tissue and mount recall responses in secondary lymphoid organs. When activated, lymphocytes proliferate, which expands the population of clones of antigen specific lymphocytes as part of the immune response. The new, antigen specific lymphocytes will be either effector cells or memory cells that are available for response in the event of a later exposure. Immune memory enables the use of immunogenic compositions as vaccines.

Also as described above, the matrix protein, along with the Pr55$^{gag}$, control (1) nuclear targeting signal of the matrix protein; and (2) the strong localizing signal to the cell plasma membrane of Pr55$^{gag}$ (Lee, Young-Min, et al., J. of Virology, pp 9061-9068 (November 1998)) The myristic acid moiety attached to the terminal end of the matrix protein is clearly critical for Gag membrane binding. Mutations of myr-MA in HIV-1 can lead to an aberrant accumulation of myr-Gag in the nucleus, and mutations at proximate sites have been shown to reduce Gag membrane binding. (Tang, Chun, Proc. Nat'l Acad. of Sci. 101: 517-522 (January 2004)) In addition, the amino acid sequence of the 10 amino acids at the N-terminal region of the MA molecule has been sequenced: GARASVLSGG (SEQ ID NO: 1). Thus, the HIV virus is not able to actively replicate infectious virions if mutations occur within this 10 amino acid sequence. (Ono, 1999) (Resh, 2004) Therefore this amino acid sequence (SEQ ID NO: 1) is highly conserved, and can be used for subunit vaccines, recombinant vaccines, naked nucleic acid vaccines and mRNA vaccines (SEQ ID NOS: 2-3).

B. Subunit Compositions

The present subunit immunogen is comprised of a peptide or portions thereof (SEQ ID NO: 1), or the genetic sequences encoding for the protein or protein segments (SEQ ID NOS: 2-3) in order to create an immune response and immune memory. In the present invention, the desired immune response is directed to the GARASVLSGG peptide (SEQ ID NO: 1), or portions thereof or the encoding genes (SEQ ID NOS: 2-3). Importantly, the composition should be presented properly to the immune system. Isolation and use of nucleic acids, peptides, and proteins are familiar to those of ordinary skill in the art, and as described herein.

One of the advantages of a subunit composition is a lack of infectivity in therapeutic applications. Therefore subunit compositions may serve when a virus is extremely virulent, as with HIV. Some viruses such as HIV undergo profound mutation and therefore an attenuated strain used in a vaccine or therapy can undergo spontaneous reversion to a more virulent strain. Therefore with HIV the use of live viral vectors would be risky. Also subunit compositions or vaccines can be used when the virus cannot be grown conveniently in culture. Subunit compositions may be produced quickly and relatively inexpensively.

For example, a subunit vaccine is currently available using the hepatitis B virus surface antigen obtained by expression of a cloned gene in yeast cells. This vaccine has been successfully used in Taiwan and it appears to have reduced the incidence of primary liver cancer in young children. (Wagner, 1999)

Direct administration of a protein would not induce a cell-mediated response in the same way that a live virus vaccine would. Yet the advantages of a subunit vaccine include a lack of potential infectivity, either mild in the case of an attenuated strain or severe in the case of the virulent strains. Further, the present invention is contemplated for use in conjunction with immune stimulants and other immunogenic compositions.

A strong stimulation of B cells and an antibody response are evident against all of the major HIV proteins soon after infection. (Goudsmit, 1988) For unknown reasons, this does not lead to the production of protective or effective neutralizing antibodies. On the contrary these antibodies may enhance uptake of HIV by cells other than CD4 lymphocytes, and thereby promote a more efficient localization in the antigen presentation cells (APC), due to deposition of complement fragments on the virus surface. (Stoiber, 1997) In the conversion of neutralizing antibodies into enhancing antibodies, follicular dendritic cells may play an important role. So far, efforts to generate effective neutralizing antibodies by vaccination have been unsuccessful. (Cohen, P. T., et al., The AIDS Knowledge Base, Ch 22 (3rd ed. 1999))

Thus, the composition of the present invention includes a method for inducing an immune response in an animal, including preferably a human. The method comprises preparing the composition and administering to an animal capable of mounting a humoral or a cellular immune response. An immune response may be detected using common methods of measurement known in the art. The present invention may be used to develop laboratory tools, and research immune response. Furthermore this invention will aid the development of a vaccine for administration to an HIV infected subject or for producing an immune response in a subject that is not infected, but for whom an immune response is desired.

C. Method of Preparation

Figure 1:
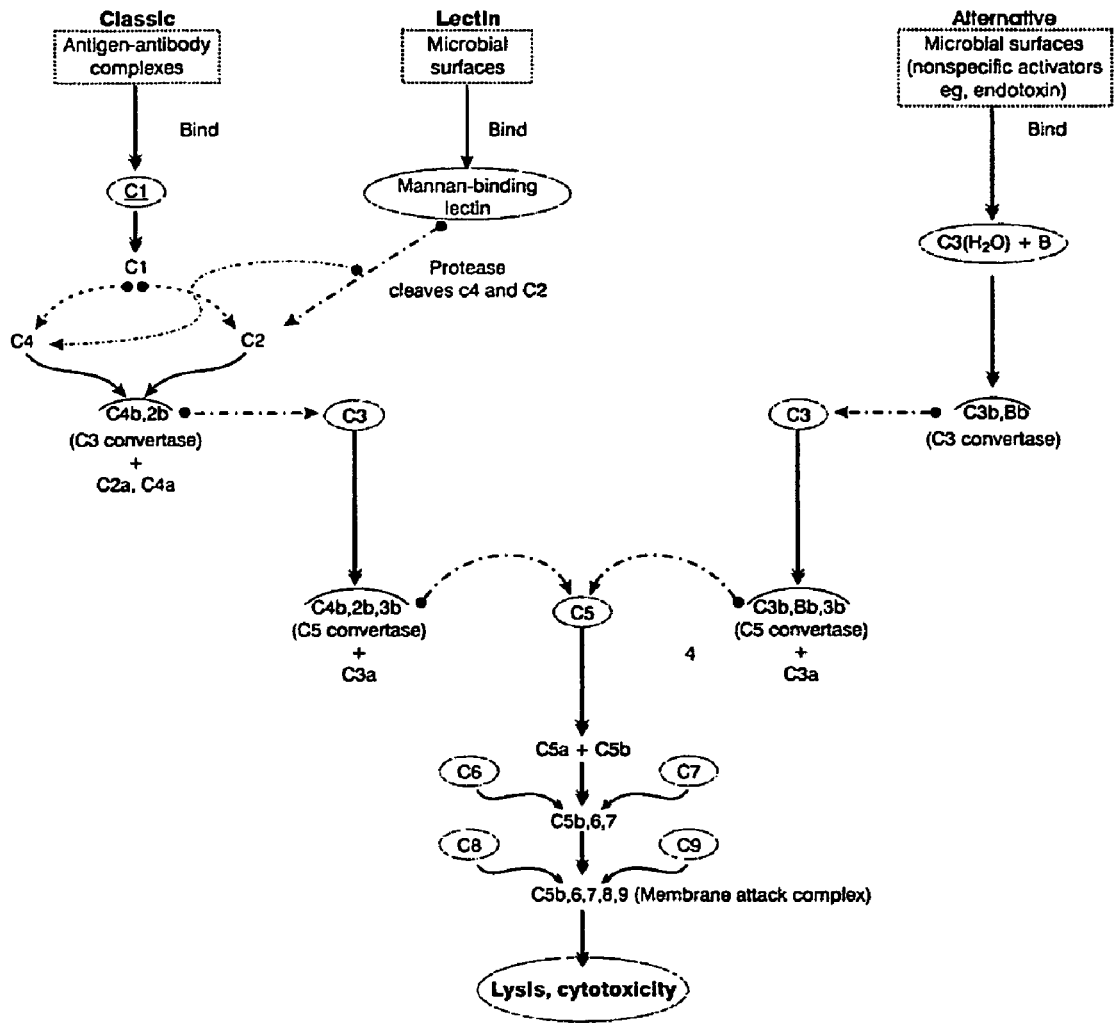
Figure 2:
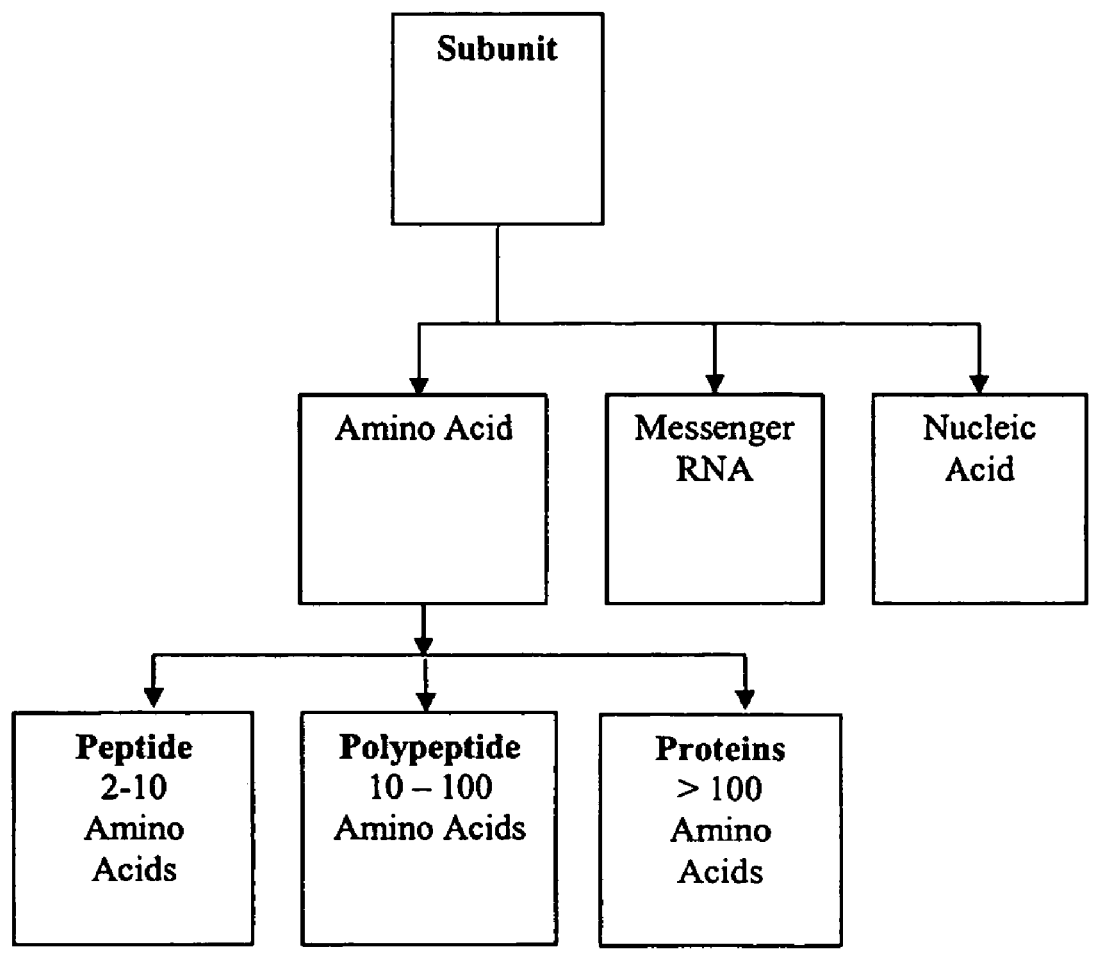

A variety of methods of development, preparation, and administration are contemplated by the present invention. It is expected that such methods shall be selected based on efficacy for the particular strain and response of the subject animal. As shown in FIG. 2 this subunit composition may be categorized for preparation purposes as protein or peptide isolation, messenger RNA, or nucleic acid DNA/RNA expression. Thus, matrix protein includes matrix protein peptides or portions (SEQ ID NO: 1), and genetic expression or material thereof (SEQ ID NOS: 2-3).

Thus, the present invention may be prepared using any one or more of a variety of methods available to those in the field, including but not limited to:

1. Purification and isolation of the covalent binding site for myristate (SEQ ID NO: 1) on the HIV matrix protein, including the amino terminal end of the matrix protein (p17MA);
2. Messenger RNA cloning expressing the covalent binding site for myristate (SEQ ID NO: 2) on the HIV matrix protein, including the amino terminal end of the matrix protein (p17MA); or
3. Recombinant DNA/RNA cloning and expression of covalent binding site for myristate (SEQ ID NOS: 2-3) on the HIV matrix protein, including the amino terminal end of the matrix protein (p17MA) into a suitable bacteria such as *escherichia coli*, or yeast, or virus, or naked DNA/RNA of the covalent binding site for myristate (SEQ ID NOS: 2-3) on the HIV matrix protein, including the amino terminal end of the matrix protein (p17MA). (Aroeti, 1993)

Antigen presenting cells take up exogenous proteins by phagocytosis, leading to presentation of the immunogen and immune response. With reference to the list above, embodiment 1 relies on protein fragments (SEQ ID NO: 1), while embodiments 2-3 rely on nucleic acids (SEQ ID NOS: 2-3) and recombinant technology. Embodiments 2-3 may also include the synthetic in vitro manufacturing of the nucleic acid (SEQ ID NOS: 2-3). (Aroeti, 1993)

C.1. Protein Based Compositions

The epitope of the protein (SEQ ID NO: 1) may be isolated from a single viral particle or a viral culture. In the case of a single particle, enzymatic (proteolytic) degradation may be used. For example, a mature protein may be isolated from viral particles by degrading and enzymatically digesting the mature viral particles into individual protein components. "Purification" means merely that the protein is sufficiently free of other cell subunits or contaminants so as to enable therapeutic use. The composition need not be totally pure. The protein portion may also be isolated from a viral culture. Each protein of the viral structure is produced in quantities exceeding that necessary for viral replication. Therefore, individual viral proteins may be isolated and separated from viral isolates based on that protein's characteristic size, shape, solvency characteristics, electrostatic potential, density and/or buoyancy and sedimentation rate in a variety of media. Therefore, this approach involves the use of specific protein fragments or peptides to elicit an immune response.

C.2. Nucleic Acid Based Compositions

In general, nucleic acid based compositions may comprise naked DNA/RNA, recombinant DNA/RNA, or messenger RNA (SEQ ID NOS: 2-3). A composition based on naked DNA would use the DNA of the viral antigen encoding the binding site that has been stripped of histones (small unfolded chromosomal proteins) or protein, usually by exposure to detergents or phenols. Recombinant DNA is genetically engineered DNA made by recombining fragments of DNA from different organisms, as discussed in detail below. DNA/RNA or mRNA for both embodiments may be isolated, purified, and amplified using procedures that are known in the art, and are partially described herein.

In addition, and as described below, mRNA based immunogenic compositions and vaccines may be an alternative concept to using naked DNA/DNA or rDNA sequence coding for protein. Messenger RNA is an intermediary between the two (DNA and protein), and can be used to transfect cells and undergo translation within a host cell to produce the viral proteins in question.

C.2.1. Isolation of DNA and RNA

Procurement of nucleic acid(s) requires three basic steps (1) lysing of the cells to expose the nucleic acids preferred for processing; (2) separation of the nucleic acids from other cell components; and (3) recovering of the nucleic acid in purified form. (Nicholls, Desmond, An Introduction to Genetic Engineering, Ch. 3 (2d ed. 2002)) "Purification" means merely that the nucleic acid is sufficiently free of other cell subunits or contaminants so as to enable therapeutic use.

A plethora of modalities may be used to recover nucleic acids. Many are quite simple requiring only a few steps. More complex purification procedures involving several different stages are standard in the industry. Commercially available kits readily enable purification of nucleic acids from a range of sources.

The first step in any isolation protocol is disrupting the starting material. The method used to open cell walls should be as gentle as possible, preferably utilizing enzymatic degradation of cell wall material and detergent lysis of cell membranes. If more vigorous methods of cell disruption are required, there is the danger of sheering large DNA molecules and this can hamper the production of representative recombinant molecules during subsequent processing.

Following cell disruption, cell proteins are removed. Phenol or phenol/chloroform mixture is often used in the extraction procedure. Upon centrifugation to separate the phases, protein molecules partition into the phenol phase and accumulate at the interface. Due to their inherent hydrophilicity nucleic acids remain mostly in the upper aqueous space and may be precipitated from solution using isopropanol or ethanol.

If a DNA preparation is required, the enzyme ribonuclease (RNase) can be used to digest the RNA in preparation. If mRNA is needed for the cDNA synthesis, a further purification can be performed using oligo(dT)-cellulose to bind to the poly (A) tails of eukaryotic mRNAs. This gives substantial enrichment for mRNA and enables most contaminating DNA, rRNA and tRNA to be removed.

Gradient centrifugation is frequently used to isolate DNA, particularly plasmid (pDNA). DNA is dissolved into a caesium chloride (CsCl) solution and spun at high speed in an ultracentrifuge. Over time (in some cases up to 48 hours) a density gradient is formed. The pDNA forms an easily identifiable band or line at one position in the centrifuge tube. This band is devoid of cellular contaminants and may be removed. Using dialysis, the CsCl is removed to give a pure preparation of pDNA. Size exclusion chromatography can be used as an alternative to ultracentrifugation. Many plasmid DNAs however, are commercially available. (Nicholls, 2002)

Amplification of a preferred DNA sequence can be accomplished by the polymerase chain reaction (PCR). (Nicholls, 2002). Simplicity, elegance and high specificity characterize PCR, which has replaced traditional cloning methodology. In the PCR process the DNA duplex is heated, thereby denaturing and unwinding the double helix and separating the strands. Each single strand is copied by a DNA polymerase.

The process is repeated many times resulting in an exponential increase in the number of copies.

C.2.2. Recombinant Technologies

Figure 3:
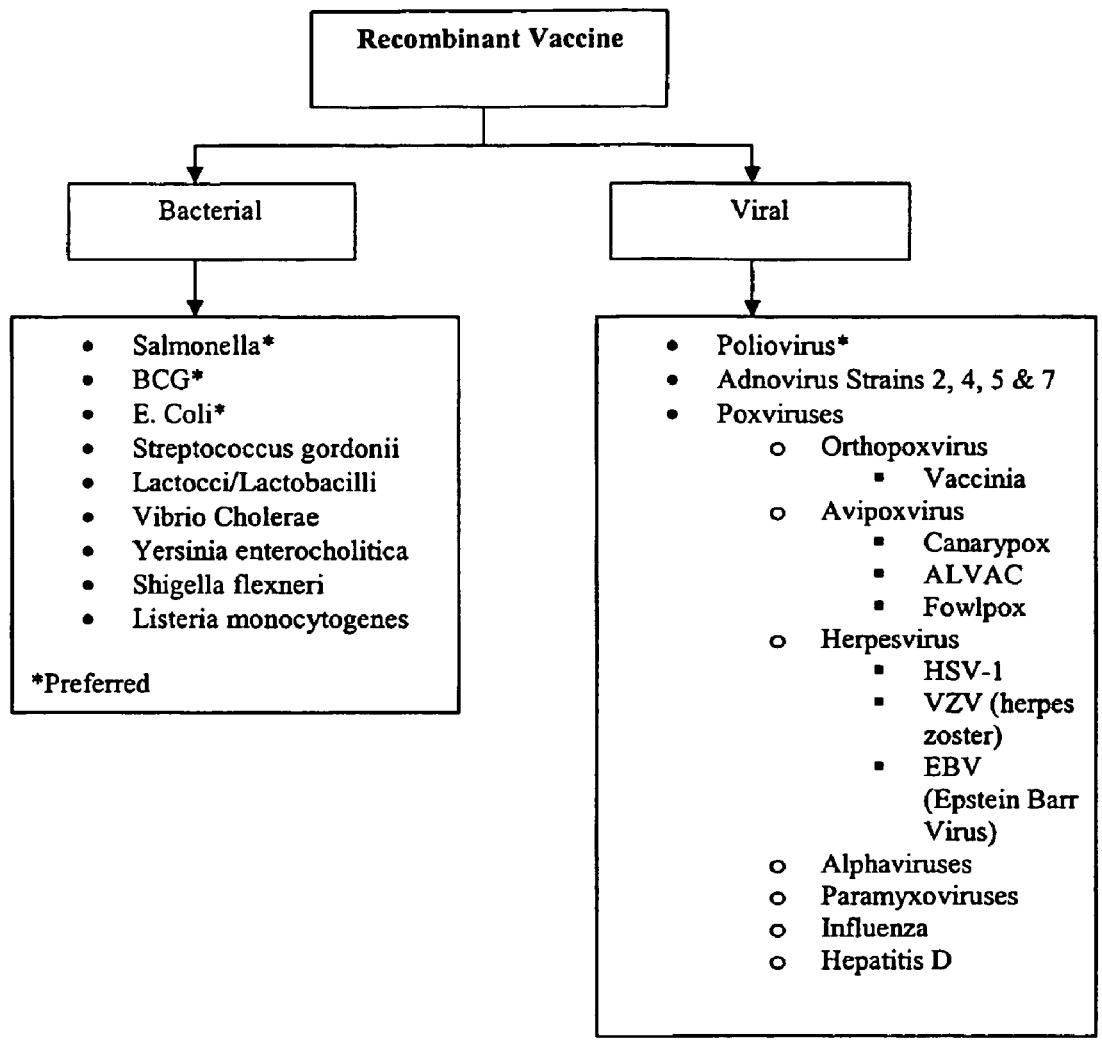
FIG. 3 is a graphic of the exemplary carriers available for recombinant DNA.
Figure 4:
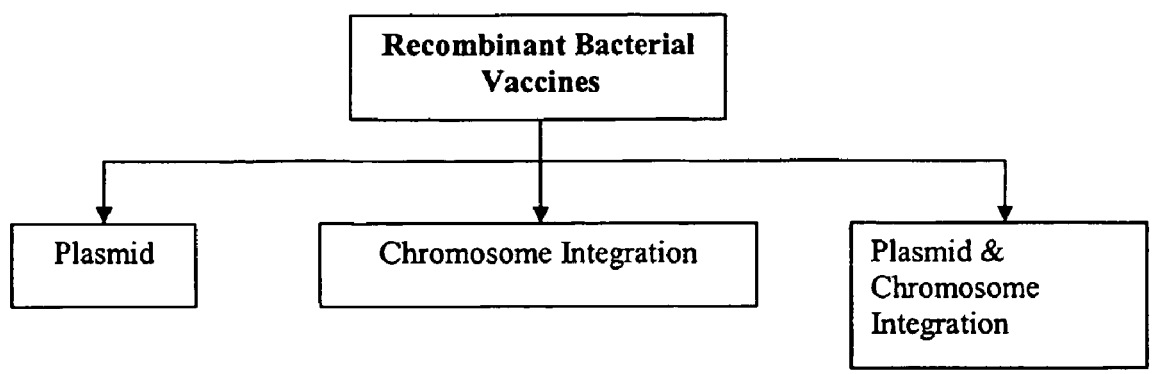
FIG. 4 is a chart that demonstrates splicing of genetic material encoding the genetic material for the matrix protein covalent binding site for myristate into recombinant bacterial compositions or vaccines.
Figure 5:
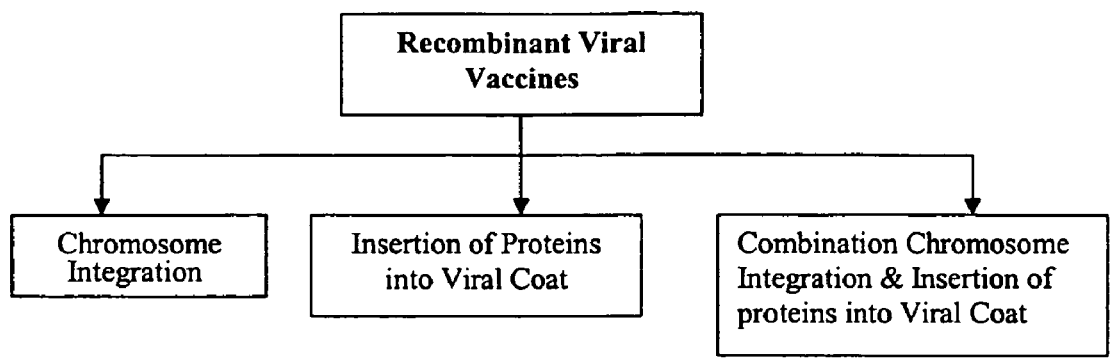
FIG. 5 is a chart that demonstrates splicing of genetic material encoding the genetic material for the matrix protein covalent binding site for myristate into recombinant viral compositions or vaccines.

The methods used in producing recombinant DNA are conceptually straightforward and known in the art. Genes of the HIV matrix protein (SEQ ID NOS: 2-3) may be engineered into the DNA of a carrier, such as *Escherichia coli*; a list of suggested carriers is in FIG. 3. As shown in FIG. 4 bacterial carriers may include rDNA by plasmid, chromosome integration, or a combination. As shown in FIG. 5, viral carriers may support rDNA by chromosome integration, insertion of proteins encoded by the donor DNA into the viral coat, or a combination. When the carrier reproduces, the immunogen is propagated if the immunogen is inserted into the host chromosome. Plasmid DNA can undergo replication within a non replicating cell. The cutting or isolation of the genes with restriction enzymes is as described herein and known.

Preparation of rDNA

Electrophoresis enables the separation, identification, and purification of DNA fragments. The porosity of the matrix determines the degree of separation achieved. Two gel types are commonly used in the field, agarose and polyacrylamide. Agarose, extracted from seaweed, is available commercially as a dry powder, which is melted in buffer at an appropriate concentration. On cooling, agarose sets or gels. Polyacrylamide gels are used to separate small nucleic acid molecules because the pore size of polyacrylamide is smaller than agarose. Polyacrylamide can separate DNA molecules that differ in length by only one nucleotide. Electrophoresis may be carried out by placing nucleic acid samples in a gel and applying an electrical potential across it. DNA contains negative charged phosphate groups and will therefore migrate towards the positive electrode. When a marker dye, usually bromophenol blue (added to the sample prior to loading), reaches the end of the gel the electrical potential is removed. The nucleic acids in the gel may be visualized by staining with the intercalating dye ethidium bromide and examined under UV light. (Nicholls, 2002) Large DNA fragments containing as many as 100,000 base pairs can be separated by another process known as pulsed gel electrophoresis.

Pulsed field gel electrophoresis (PFGE) and simple gel electrophoresis permit DNA fragments to be separated on the basis of size: the smaller the fragment, the more rapid the migration. Overall rate of migration and optimal range of size for separation are determined by the chemical nature of the gel and by the degree of its cross-linking. Highly crossed linked gels optimize the separation of small DNA fragments. The dye ethidium bromide forms a brightly fluorescent adduct as it binds to DNA. Small amounts of separated DNA fragments can be isolated on gels. This dye binds between the DNA bases (intercalates) and fluoresces orange when illuminated with ultraviolet light. (Nicholls, 2002) The identification of a specific DNA fragment can be accomplished by probes containing complementary sequences.

All methods of electrophoresis rely on the polyanionic nature of nucleic acids (RNA & DNA, single stranded and double stranded) at neutral pH, i.e., nucleic acids carry multiple negative charges on the phosphate groups. This means that the molecules will migrate towards the positive electrode when placed in an electric field. As negative charges are distributed evenly along the DNA molecule, the charge/mass ratio is constant, thus mobility depends on fragment length. The technique is preferably executed on a gel matrix which separates the nucleic acid molecules according to size. (Nicholls, 2002)

Restriction enzymes or endonucleases allow bacteria to distinguish between homologous and heterologous DNA. These enzymes hydrolyze and cleave DNA at specific sites known as restriction sites. This specificity of sequence recognition allows the precise selectivity of DNA fragment preparation, which is the foundation for DNA vaccines. Bacteria that possess a restriction enzyme system disguise recognition sites in its own DNA by modifying them. The addition of a methyl group to an adenine or cytosine residue near or at the site of cleavage protects its own nucleic acid. (Brooks, Geo., Medical Microbiology 102 (23rd ed. 2004))

Restriction modification systems of bacteria fall into two broad classes: Type 1 systems in which the restriction and modification activities are combined in a single multi-subunit protein, and Type 2 systems which consist of separate endonucleases and methylases. (Brooks, 2004)

An analogy between restriction endonucleases that have become standard laboratory devices and a surgeon's knife is evident. Restriction endonucleases are usually named by a three or four letter abbreviation of the named organism from which the enzyme has been isolated. (Brooks, 2004) The generic and specific names of the organism in which the enzyme is formed are used to provide the first part of the designation which comprise the first letter of the generic name and is the first two letters of the specific name. Thus an enzyme from the strain of *Escherichia coli* is termed Eco and one from *Bacillus amyloliquefaciens* is Bam. (Nicholls, 2002)

Restriction endonucleases generally cleave phosphodiester bonds in both DNA strands in a mirror like fashion. A restriction enzyme recognizes and cleaves at the same DNA sequence and only cleaves at that particular sequence. Most of the DNA sequences recognized by restriction enzymes are palindromes; that is, both strands of DNA have the same basic sequence running in opposite directions on either side of the axis of symmetry when read in a 5' to 3' direction (self-complementary). The cuts made by these enzymes are usually "sticky" (i.e., the products are single-stranded at the ends with one strand overhanging the other.) However, sometimes the products are blunt with double stranded ends. Over five hundred restriction enzymes with different specificities have been isolated and characterized. Most are readily available as laboratory tools.

Restriction fragments of DNA may be used to identify variations in base sequence in a gene. However they can also be used to synthesize a recombinant DNA also called chimeric DNA, which is composed of molecules of DNA from different sources that have been recombined in vitro. The sticky ends of two unrelated DNA fragments may be joined to each other if they have complementary sticky ends. Complementary ends may be obtained by cleaving unrelated DNAs strands with the same restriction enzyme if the restriction enzyme recognizes palindromic strands. After the sticky ends of the fragments base pair with each other, the fragments can then be covalently attached by the action of a DNA ligase. (Smith, Coleen, Basic Medical Biochemistry: A Clinical Approach, Ch. 17 (2d ed. 1996)) DNA ligase is a cellular enzyme that repairs broken phosphodiester bonds that may occur at random or as a consequence of DNA replication or recombination. (Nicholls, 2002) The DNA ligase most often used is T4 DNA ligase, which may be purified from *E. coli* cells infected with bacteriophage T4. Although the enzyme is most efficient when sealing gaps in fragments that are held together by cohesive ends, it will also join blunt-ended DNA molecules together under appropriate conditions. DNA ligase produces a phosphodiester bond between a 5' phosphate and a 3' hydroxyl (OH) group. The enzyme is most effective at 37°

C., but may be used at lower temperatures. Thermodenaturation of the single strand ends however, occurs at higher temperatures (37° C.). Therefore this enzymatic process if often accomplished at lower temperatures to affect a higher purity although the overall process is somewhat slower. (Nicholls, 2002)

The length of DNA fragments produced by restriction enzymes varies tremendously because of the individuality of DNA sequences. Most restriction enzymes recognize palindromic sequences which occur somewhat randomly. Furthermore the average length of a DNA fragment is determined, in large part, by the number of specific base pairs recognized by the restriction enzyme. Restriction enzymes recognizing up to 15 base sequences have been characterized, however most recognize four, six, or eight base sequences. Recognition of four bases yields fragments with an average length of 250 base pairs, and therefore is generally useful for analysis or manipulation of gene fragments. As the number of base pairs recognized by the restriction enzyme increases the average length of the nucleotide sequence increases logarithmically. For instance restriction enzymes that recognize six bases produce fragments with an average size of about 4,000 base pairs. Restriction enzymes that recognize eight bases produce fragments with a typical size of 64,000 base pairs and are therefore useful for analysis of larger genetic regions. (Brooks, 2004)

In the production of DNA vaccines, plasmid DNA derived from eukaryotic cells such as bacteria and yeast is often used as the donor vehicle. A plasmid is a genetic particle physically separate from the nucleus of the host cell. The nuclei of prokaryotes are not enveloped. Plasmid can independently function and replicate, that is independent of the nucleus of the cell. Plasmids usually confer some survival or growth advantage to the host cell, but are not essential to the cell's basic function. For example, a resistance plasmid carries genes responsible for antibiotic or antibacterial drug resistance. Plasmids are small circles of DNA; however the three dimensional structure is often that of a figure eight or more complex structure. Nonetheless, the small size of plasmids renders them amenable to genetic manipulation in vitro. Furthermore, after genetic manipulation their small size permits introduction into other cells. Therefore, plasmids are frequently used in genetic engineering and are the basis of most DNA vaccines. (Brooks, 2004)

Because many restriction enzymes cleave asymmetrically and produce DNA fragments with cohesive (sticky) ends, hybridization of DNA is possible. This DNA can be used as a donor with plasmid recipients to form genetically engineered recombinant plasmids. Cleavage of a plasmid with the same restriction enzyme produces a linear fragment with cohesive ends that are identical to each other. To prevent the two ends of the plasmid from reannealling enzymatic removal of the free phosphate groups from these ends is performed. This ensures that the original circular plasmid is structurally incompetent and cannot function. Ligation in the presence of other DNA fragments from other sources containing free phosphate groups produces recombinant plasmids or chimeric plasmids which contain DNA fragments as inserts in covalently now circular DNA. Plasmids must be in a circular form in order to replicate in the bacterial host. (Brooks, 2004)

The amino acid sequence of the present subunit, the amino terminal end of the matrix protein (p17MA) and the covalent binding site for myristate (SEQ ID NO: 1) on the HIV virus, has been deduced. Each amino acid is coded by a separate codon. A codon is a set of three consecutive nucleotides in a strand of DNA or RNA that provides the genetic information to code for a specific amino acid which will be incorporated into a protein chain or serve as a termination signal. Therefore, knowledge of the present subunit permits deduction of the nucleotide sequence of the DNA and/or RNA for the amino terminal end of the matrix protein (p17MA) and the covalent binding site for myristate (SEQ ID NOS: 2-3) on the HIV virus. The origin for elongation of a DNA sequence is determined by a DNA primer that can be synthesized by known nucleotide synthesizing devices for chemical oligonucleotide synthesis. Such devices can produce DNA strands containing 75 or more oligonucleotides. (Brooks, 2004)

Chemically synthesized oligonucleotides can serve as primers for polymerase chain reaction (PCR) which is a procedure that allows amplification and sequencing of DNA between the primers. Thus, in many instances, DNA need not be cloned in order to be sequenced or to be made available for engineering.

DNA sequencing can also be performed using the Maxam-Gilbert technique, which relies on the relative chemical liability of different nucleotide bonds and the Sanger (dideoxytermination) method, which disrupts the elongation of DNA sequences by incorporating dideoxynucleotides into the sequences. Furthermore a procedure known as shotgunning allows the sequencing and analysis of entire genomes in viruses. In this procedure, DNA is randomly fragmented to create a random fragment library. These unordered fragments are sequenced by automated DNA sequencers and may be reassembled in correct order using computer software available in the field. (Brooks, 2004)

The essential components of a plasmid DNA designed for vaccination include a start signal (promoter-enhancer) and stop signal (polyadenylation signal/transcript termination sequence). The start and stop signals can be selected from a variety of sources viral, bacterial or mammalian. A marker of activity of the plasmid such as antibiotic resistance or specific enzymatic activity can be included and may be advantageous if only to demonstrate that a fully functional plasmid has been developed. It is also advantageous to include intron-containing sequences that have been shown to greatly improve expression within transfected cell lines for many constructs even through introns contain sequences that are ultimately not translated into protein. The promoters/enhancers that have been mostly used for DNA vaccines are the CMV immediate early promoter (pCMVIE) enhancer and the Rous sarcoma virus (RSV) LTR. Hundreds of plasmids are available commercially from different suppliers. A basic plasmid vaccine vector is known as V1J. This is comprised of pCMVIE, intron A derived from CMV, bovine growth hormone (BGH) polyadenylation/transcript termination sequence and a gene ($amp^r$) coding for ampicillin resistance. A pUC plasmid DNA sequence from which the lac operon and multicloning site have been deleted, serves as the basic construct for this recombinant plasmid structure. Two separate restriction enzyme sites have been mapped for insertion of donor DNA. V1J does not replicate in mammalian cells and does not contain any sequences known to promote plasmid integration into host genomic DNA ensuring a wide safety margin. Furthermore it can be produced in large quantities by growth in *E. coli*. These properties help ensure the safety of the recombinant DNA process by minimizing the probability for cell-transforming integration events.

Best results for vaccination in animals have been obtained by using normal saline solutions of plasmid. Other vehicles including solutions of bupivicaine and sucrose have been used, but there has been no enhanced immunogenicity with these methodologies in animals. (Kaufman, Stefen, Concepts in Vaccine Development, ch 3.7.3, (1996)) A small percentage of myotubules take up and express DNA following intramuscular injection of a plasmid saline formulation. This however, has been sufficient for obtaining significant immune responses. (Kaufmann, Stefan, Concepts in Vaccine Development Ch. 3.7 (1996))

Both humoral and cytotoxic T cell responses are noted to occur with naked DNA vaccines. Strong proliferation of T cells was observed at low DNA doses in animal models down to one microgram even in the absence of measurable antigen-specific serum antibody responses, indicating that less antigen may be required to elicit T cell responses by DNA vaccines than for antibody generation. Therefore, since the most likely correlate of immunity to HIV disease would be a robust cytotoxic T cell response directed toward HIV disease, less (antigen) with HIV vaccine technology means more. The development of a strong humoral response to HIV disease has been associated with a poorer prognosis. Low dose DNA vaccines stimulate the production of Type 1 helper T cells Th-1. $T_H1$ cells generate cytokines Il-2 and gamma-interferon which have been shown to promote cellular immune responses by stimulating $CD8^+$ activity. (Kaufmann, 1996) Thus, a selective and substantial or predominant Th-1 immune response, as described above, is desirable.

For HIV infections, strong $T_H1$-like responses have been important in maintaining high CD4 cell counts and low viral titers as well as prevention of secondary opportunistic infections. (Kaufmann, 1996)

The advantages of expressing antigens in the host rather than administering antigens such as inactivated viruses, recombinant proteins or peptides, include the following: (1) circumventing potential loss of antigenicity by an inactivation process (e.g., chemical cross linking) inherent in the host cell; (2) synthesis of proteins with conformation and post translational modifications including carbohydrate and lipid linkages encoded by the host cell; (3) intracellular antigen processing and presentation by MHC class I molecules leading to the induction of cytotoxic T lymphocyte (CTL) responses; and (4) allowing for MHC determinant selection. (Kiyono, Hiroshi, Mucosal Vaccines Ch. 8 (1996))

Antigen presentation after IM DNA vaccination results in a robust cytotoxic T cell response. Three models for inducing the CTL response with IM DNA vaccines have been proposed:

1. Uptake of DNA and expression of antigens by antigen presenting cells including dendritic cells, macrophages and langerhans cells;
2. Antigen presentation by transfected myocytes acting as or assuming the role of antigen presenting cells; and
3. Transfer of antigens from transfected myocytes to antigen presenting cells which in turn present the antigen to the appropriate T cell. (Kiyono, 1996)

DNA vaccines have been used to elicit specific immune responses, antibody, CD8 cell and CD4 cell, against a variety of antigens in animal species, including but not limited to the following:

1. Hepatitis B surface antigen in mice (Davis, et. al., 1993, 1994)
2. Herpes simplex virus 1 glycoprotein B in mice (Manickan et. al., 1995)
3. Bovine herpesvirus 1 glycoprotein IV in cattle (Cox et. al., 1993)
4. Rabies virus glycoprotein in mice (Xiang, et. al., 1994, 1995)
5. Malaria circumsporozoite protein in mice (Sedegah, et. al., 1994; Hoffman et. al., 1994)
6. *Leishmania* gp63 in mice (Xu and Liew 1995)
7. Lymphocytic choriomeningitis virus (LCMV) NP in mice (Pedroz Martins, et al. 1995; Yokoyama et. al., 1995)
8. Carcinoembryonic antigen in mice (Conry, et. al., 1994)
9. MHC class I antigen in rats (Geissler, et. al., 1994)
10. Cottontail rabbit papillomavirus (CRPV) L1 in rabbits (Donnelly et. al., 1996)
11. *M tuberculosis* antigen 85 complex proteins in mice (Huygen et. al., 1996) (Kaufmann, 1996)

More specifically, the ability of DNA vaccines to induce CTL responses has also been demonstrated several times. It was first demonstrated using influenza NP (nucleoprotein). NP is a conserved internal protein of the virus and a target for cross reactive CTL. The NP DNA induced a CTL response in mice which demonstrated an element of longevity implying the potential for vaccination. Interestingly cell mediated immunity induced by DNA encoding influenza NP or matrix protein also played a role in protection of ferrets as measured by reduction of virus shedding in nasal secretions. DNA vaccine induced CTL response has been demonstrated for the following as well:

1. Rabies virus glycoprotein (Xiang, et al., 1994)
2. Malaria circumsporozoite protein (Sedegah, et al., 1994)
3. Lymphocytic choriomeningitis virus NP (Pedroz Martins, et al., 1995; Yokoyama, et. al., 1995; Zarozinski et al., 1995)
4. HIV envelope protein (Wang, et al., 1994; Shiver et al., 1995)
5. Human Factor IX (Katsumi, et al., 1994)
6. MHC class I (Geissler, et al., 1994; Plautz, et al., 1994; Hui et al., 1994)

Detection of CTL responses for one to two years after immunization has been noted in some of the above models. Dosing of the DNA vaccine should start at 1 mcg. CTL assays should be performed and the lowest dose at which an adequate CTL response is noted is a preferable dose for administration.

As discussed below, cationic lipids formulated with IM DNA vaccine actually resulted in a lower level of gene expression. However, the use of cationic lipids to facilitate DNA uptake has been noted with mucosal delivery systems. Cationic lipids facilitate DNA uptake on mucosal surfaces via a non-specific mechanism or a specific plasma membrane transport mechanism yet to be characterized. Mucosal delivery of DNA can potentially transfect many cell types lining the GI and GU tract as well as the cells beneath their respective basement membranes including Peyer's patches which are preferred sites of HIV replication. In addition to potential facilitation of cellular uptake on mucosal surfaces, cationic lipids also protect DNA from degradation. In vitro studies have shown that DNA/cationic lipids have a longer half life than uncomplexed DNA. (Puyal, et al., 1995) Therefore the preferred embodiment for mucosal DNA vaccines will include cationic lipids.

Parenteral administration of DNA vaccines induces strong systemic humoral and cell mediated immune responses (dose dependent), but does not result in the generation of significant mucosal immune responses. Therefore in certain instances it may be desirable to design a vaccine that could induce both mucosal and systemic immune responses. (Kiyono, 1996) This can be achieved by DNA vaccines delivered by different routes (parenteral and mucosal). This approach has been tested in several systems using parenteral priming followed by mucosal boosting (Keren, et al., Infect. Immun., 56: 910-915 (1988)) and vice versa (Forrest, et al., Infect. Immun. 60: 465-471 (1992)). With some vectors mucosal administration of DNA/cationic lipids resulted in both local and systemic immune responses. A recombinant BCG vaccine induced local IgA and serum IgG antibodies against heterologous antigen (Langerman, et al., 1994) and a recombinant *Salmonella* vector given orally induced cell mediated immunity (Aggarwal, et al., 1990).

A preferred embodiment utilizing DNA vaccine technology would be a combination of a naked DNA vaccine administered parenterally (preferably intramuscularly) and a cationic lipid/DNA vaccine applied mucosally.

Therefore in summary, to produce a recombinant bacteria DNA vaccine, the following steps will be followed:
1. Selecting a suitable plasmid vector from commercially available sources
2. Isolating the subject HIV DNA
3. Effecting restriction enzyme cleavage/modification of plasmid DNA and HIV DNA
4. Isolating the specified gene(s) from HIV
5. PCR amplifying selected HIV DNA gene(s)
6. Enzymatically removing free phosphate ($PO_4$) groups from plasmid DNA
7. Transforming the plasmid DNA into a bacterial cell such as *E. coli.*
8. Administering ligase to seal the DNA strands together To accomplish the process of transformation the recipient cells need to be made competent. Competence relates to the ability of a cell to assimilate foreign RNA or DNA. The steps to accomplish this are:

1. Soaking the recipient cells in an ice cold solution of calcium chloride (this induces competency in a way that is still not fully understood);
2. Mixing the plasmid DNA with the cells and incubating them on ice for 20 to 30 minutes;
3. Heat shocking (two minutes at 420° C.) to enable the DNA to enter the cells;
4. Incubating the transformed cells in a nutrient broth at 37° C. for 60 to 90 minutes. This allows the plasmid to become established and ultimately permit phenotypic expression of the plasmid nucleic acid; and
5. Placing the cells with the plasmid vector onto a selected media suitable for replication.

As shown in FIG. 3, rDNA/RNA may be delivered by a bacterial or viral carrier.

C.2.3 Recombinant Carriers

C.2.3.1 Bacterial Carriers

Live attenuated bacteria may serve as carriers for DNA/RNA. Bacteria may carry and express genes that are encoded with the amino terminal end of the matrix protein (p17MA) and the covalent binding site for myristate (SEQ ID NOS: 1-3) on the HIV virus on the matrix protein or portions thereof. The bacteria provide an environment in which the capsid protein DNA/RNA may be amplified, purified and administered. Bacterial carriers may include those customary in the art, exemplary types being *Salmonella*, BCG, *E. Coli, Streptococcus gordonii, Lactococci/Lactobacilli, Vibrio Cholerae, Yersinia enterocolitica, Shigella flexneri*, and *Listeria monocytogenes*. *Salmonella*, BCG, and *E. coli* are preferable.

Among the bacteria thus far explored for recombination, attenuated *Salmonella* sp. has received the most intense scrutiny. Other bacteria including *Bacillus* Calmette-Guerin (BCG) have also been investigated. Attenuated enteric pathogens including *E. coli, Vibrio, Yersinia* and *Shigella* have been used as platforms for recombinant vaccine technology. Other organisms generally considered as commensals including the gram positives *Streptococcus gordonii, Staphylococcus xylosus* and the *lactococci* or *lactobacilli* have been used in recombinant methodologies. Recently *Listeria monocytogenes* has been introduced as a potential recombinant vaccine vector. Most of these organisms by virtue of their ability to colonize and/or infect mucosal surfaces lend themselves to delivery to these surfaces. Therefore the gut associated lymphoid tissue (GALT) is being stimulated directly through mucosal immunization rather than antibody diffusion from the serum subsequent to parenteral inoculation. GALT including Peyer's Patches is the primary site of HIV infection and replication in sexual transmission of the disease.

The preponderance of attention is focused on enteric pathogens, particularly *Salmonella*. The bacteria undergo the process of attenuation before recombination can occur. In doing so, the bacteria become avirulent and are unable to cause typhoid fever or other *salmonella* derived diseases. The first description of such mutation appeared in 1951 in the metabolic pathway for p-aminobenzoic acid (pab). Subsequently gal E mutants of *S. typhimurium* and *S. typhi* (strain Ty21a) were isolated which resulted in the cytoplasmic accumulation of galactose-1-phosphate leading to the lysis of cells. Hoiseth and Stocker in *S. typhimurium* introduced the widely used *salmonella* auxotrophic mutant, aro A, which encodes the enzyme 5-enolpyruvyl-shikimate-3-phosphate synthetase, an essential element in the aromatic pathway. Additional mutations made in this pathway involving aro C and aro D genes in *S. typhimurium* result in highly attenuated organisms. Mutations in the regulatory genes cya, crp which encode for adenylate cyclase and the cyclic AMP receptor protein respectively have also been proven highly successful. Furthermore the cya and the crp mutations are often used in conjunction with mutations in asd encoding aspartate gamma-semialdehyde dehydrogenase which is essential for peptidoglycan synthesis. In addition, mutations of other regulatory genes such as phoP (phosphatase) and ompR (outer membrane proteins) have proved successful as attenuators of vaccine vector strains. (Hughes, Huw, Bacterial Vectors for Vaccine Delivery, Designer Vaccines Principles for Successful Prophylaxis, Ch. 8 (1998))

Three separate methods have been used for expression of heterologous antigens in *salmonella* have been delineated: (1) plasmids; (2) integration of the foreign gene into the *salmonella* chromosome; and (3) transportation of foreign antigens to the cell surface by various carrier proteins of the *salmonella* bacteria including flagellin, *Neisseria*, IgA protease precursor, lanB, phoE, ompA. Other carriers of epitopes which target alternative cellular compartments include fusions with maltose-binding proteins (malE), LTB, the C fragment of tetanus toxin (tetC), -galactosidase, pagC and the core antigen (HBcAg) of hepatitis B. (Hughes, 1998)

Recombinant *salmonella* has been used successfully to express a number of viral antigens with induction of both humoral and cell mediated responses to the heterologous antigen in animal studies. Various proteins of influenza have been successfully expressed using the *salmonella* bacterial vector in animals, including the nucleoprotein (NP) and an epitope of the hemagglutinin protein (HA). Other viral DNA sequences have been successfully integrated into *salmonella* includes hepatitis B virus, HIV, and herpes simplex.

Most studies have used the oral delivery system for foreign antigens but others have used parenteral immunization protocols. Both can be used concomitantly or sequentially with recombinant vaccines. Other variables that need to be addressed with recombinant bacterial vaccines with HIV disease include the targeting of foreign antigens to the specific cell compartments. Interestingly, BCG and *Listeria* appear to be more advantageous for eliciting a cellular response and therefore would be the preferable routes for recombinant vaccine technology with HIV disease. (Hughes, 1998)

Using attenuated *salmonella* bacteria does have an advantage in that it initially replicates in the large intestines and immune response occurs in Peyer's patches, which are the immunologic vehicles lining the terminal colon and are the sites for initial HIV replication in most cases where the virus is transmitted sexually. Therefore *salmonella* bacteria would offer a preferred methodology for recombinant vaccine technology with HIV disease.

The techniques of transformation and transfection represent the simplest methods available for getting recombinant DNA into cells. In the context of cloning *E. coli* cells, transformation refers to the uptake of plasmid DNA and transfection to the uptake of bacteriophage DNA. A bacteriophage is a virus that infects bacteria. Like other viruses they contain either (but never both) RNA or DNA, and vary in structure from the seemingly simple filamentous bacterial virus to a relatively complex form with contractile tails. Their relationships to the host bacteria are highly specific. Transformation is also used more generally to describe uptake of any DNA by any cell. (Nicholls, 2003)

Only a small percentage of competent cells undergo transformation. Thus, the process can become the rate limiting step in a cloning experiment where a large number of individual recombinants is required or when the starting material is limited. Properly performed, $10^9$ transformed cells (transformants) per microgram of input DNA can be realized, although transformation frequencies of about $10^6$ or $10^7$ transformants per microgram are more realistic. (Nicholls, 2003)

An alternative to transformation procedures is to introduce DNA into the cell by a physical method. One exemplary technique is microinjection, or using a very fine needle and injecting the DNA directly into the nucleus. This technique has been used successfully with both plant and animal cells. The cell is held on a glass tube by mild suction, and the needle is used to pierce the membrane. The technique requires a mechanical micromanipulator and a microscope and is done by hand. (Nicholls, 2003) Microinjection offers a preferred embodiment for DNA bacterial recombinant vaccine production with HIV disease.

C.2.3.2 Viral Carriers

Recombinant viral vaccines may be engineered to express genes from the pathogen against which the host is to be protected. The vector serves as a vehicle to carry the foreign gene into the host, and after transcription and translation of the nucleic acid present the protein encoded by the nucleic acid to the immune system of the host. As with any vaccine, of course, the major criteria for acceptability are safety and efficacy. Safety may be approached from two perspectives. The safety of the immunogen can be assured by using viral vectors with good safety records due to prior attenuation or prior vaccination of the host to the carrier virus. Secondly, viruses may be engineered to improve safety in a rational and reliable manner. (Hughes, 1998) The utilization of viral vectors to which the host has already been immunized does have a disadvantage in that the immunogen would be rapidly destroyed by a memory immune response. Nonetheless some transcription and translation of recombinant DNA or RNA would occur. A preferred methodology would be use of an attenuated nonvirulent virus (without prior immunization to the carrier virus) as a carrier for the recombinant vaccine.

Thus, viruses like bacteria or yeast may also be used in recombinant technology. As carriers, viruses easily infect cells and stimulate cytotoxic T cell immune responses. Because the carrier virus may be able to replicate, a full and complete immune response may be generated. Both the humoral and cellular arms of the immune system would then be activated. General viral carriers may include Poliovirus, Adenovirus Strains 2, 4, 5, and 7, and Poxviruses. Some of the poxviruses used in recombinant technology include vaccinia, canarypox, ALVAC (derived from canarypox), fowlpox, pigeonpox, and swinepox. Other viral vectors used in recombinant technology include herpesvirus (HSV-1, VZV (herpes zoster), EBV (Epstein Barr Virus)), Alphaviruses, Paramyxoviruses, Influenza, and Hepatitis D. Of these, a preferred embodiment is based on poliovirus due to extensive existing knowledge of the virus structure and lifecycle. Prior immunization to Polio would be a consideration in limiting the immune response. Chronic viral infections such as HSV-1 offer an attractive alternative since the host immune system would receive low dose background immunogen stimulating cytotoxic activity.

The introduction of genes from one microorganism into the genome of another microorganism may result in a virulent strain. To avoid this, the carrier virus should be modified to ensure that any use of the composition in treatment is, in fact, avirulent. This would allow for a myriad of viral mosaic combinations to be developed. The gene(s) introduced may replace genes not required for replication of the carrier virus when it is used as a vaccine or it could be added to the viral genome. (Wagner, 1999) Methods for practicing recombinant technology in the production and use of immunogenic compositions or vaccines for viral infections are known and currently available to those in the field. (Porter, 1995) (Stahl, 1997)

Among the viruses used for recombinant viral vaccine vectors are pox viruses (vaccinia virus which includes fowlpox, canarypox, pigeonpox, myxoma and swinepox), adenovirus (particularly types 2 and 5 which have been sequenced and adenovirus types 4 and 7 have been widely used as vaccines, not commercially but for the U.S. military without evidence of adverse effects), herpes virus, polio virus and influenza virus. HIV genes have been spliced into vaccinia virus vectors with some limited success in animals. With adenovirus, genes can be inserted into the non-essential E3 region (up to four kb) or in the essential E1 region. Interestingly, construction of recombinant adenovirus expressing the glycoprotein B of herpes simplex virus (HSV) from the E3 region has been performed by McDermott et al. Inoculating mice with this recombinant virus produced antibodies specific for gB which neutralized HSV in vitro. In addition, mice were protected from a lethal HSV challenge after a single inoculation with the adenovirus recombinant. Jacobs, et al. have utilized the E1 region to express and non structural gene, NS1, from the tick-borne encephalitis (TBE) virus. They have demonstrated protection against lethal challenge in a murine model using this replication defective system. The E1 deleted adenoviruses have an extra safety factor introduced by their replication defective nature. The E3 gene confers immunoprotection to the virus. Therefore, recombinant adenovirus vectors missing the E3 gene are attenuated and avirulent and represent a preferred embodiment using adenoviral vectors with recombinant viral technology. The gp19 protein encoded by the E3 region reduces expression of the major histocompatibility complex (MHC) class I antigens in infected cells. The gp19 protein may act at the level of transcription, translation, protein modification in the endoplasmic reticulum or Golgi apparatus or combination thereof. Adenovirus vectors deficient in this gene may be more efficient in presenting the proteins encoded in their foreign genes to the immune system in a more effective manner eliciting a more robust CD8 cytotoxic response. Furthermore, hepatitis B surface antigen has been expressed from adenovirus strains 4 and 7, both with and without deletions of E3, and in animal models a good antibody response was noted in those vectors lacking the E3 sequences. Vectors containing a functional E3 sequence generated only weak or negligible responses. (Hughes, 1998)

Herpes viruses have a large genome and several genes have been identified as non essential in vitro and more importantly in vivo. The deletion of non-essential genes would allow recombination at several sites and allow more than one recombination event per virion. A limited number of examples of herpes virus vaccine vectors have been tested in a natural host with some success. For example, Dan Ziji, et al. has reported the protection of pigs against pseudo-rabies virus as well as hog cholera virus.

Influenza has been recently added to the list of potential viral vaccine vectors in recombinant vaccine technology. Influenza in an uncompromised host is relatively nonvirulent. Manipulation of the influenza nucleic acid can be accomplished with reverse genetics. Castrucci, et al. have constructed a recombinant influenza virus expressing a CTL epitope from the LCMV nucleoprotein in the stalk of the influenza neuraminidase enzyme which cleaves sialic acid. A single dose of this recombinant vaccine protected mice against future challenge by virulent non attenuated LCMV. Many influenza strains have been characterized, and many of those vary only in the hemagglutinin and neuraminidase proteins they express. Therefore, different influenza strains can be used sequentially to vaccinate a host to a specific viral protein without the problem of developing immunity to the viral vector itself which would limit the effectiveness of repeated inoculations. Cold-adapted attenuated influenza viruses have been used extensively for years as vaccines. Stocks of these vaccines could be used for recombinant virus vaccines, particularly if several inoculations were required.

Rodriguez, et al. tested the efficacy of recombinant influenza vectors. The $CD8^+$ T cell epitope of the circumsporozoite protein of *Plasmodium yoelii*, a rodent malaria parasite, was expressed in two distinct influenza proteins, hemagglutinin and neuraminidase in the same virion. In addition a vaccinia virus recombinant expressing only one copy of the same epitope was constructed. Both vectors systems were found to induce comparative levels of epitope-specific T cells. The most efficacious protocol consisted of priming with the influenza recombinant followed by boosting with a vaccinia recombinant. (Hughes, 1998)

Two separate recombinant viral vectors may be used sequentially or concomitantly for optimum immune response with HIV disease.

Live vaccines against polio (Sabin) are attenuated strains of the virus itself. Although these vaccines proved to be extremely safe and effective (introduced in 1961), occasional reversion to virulence complicated the methodology. The American Academy of Pediatrics endorsed the older Salk vaccine (introduced in 1955), which is not capable of active replication. However, despite its safety, the Salk vaccine produces a less competent immunologic response. Due to the tight compartmentalization of the poliovirus virion, only small DNA sequences coding for a few amino acids can be cleaved into the viral genome for recombinant technology.

Polio virus is classified as an enterovirus because of its fecal/oral transmission route. Polio is a plus stranded RNA virus as is HIV disease. To differentiate between the two, although both are positive sense RNA, the retroviruses require RNA to be converted to DNA by a virion-associated enzyme (reverse transcriptase). Polio however does not require a reverse transcription enzyme. The polio RNA functions like a cellular messenger RNA. Both viruses are encased in icosahedral structures. Polio is non-enveloped; HIV however is an enveloped virus.

Polio-specific cellular immune responses have recently been studied. The generation of a cell mediated response to the polio virus has been demonstrated in orally vaccinated volunteers. (Simmons, et al., 1993; Graham et al., 1993) This is important because as mentioned before, T cell immunity will be the best correlate with immune protection to HIV disease. (Kiyono, 1996)

Interestingly, the polio virus can be delivered not only orally but nasally to stimulate both the systemic and mucosal antibodies. The development of a recombinant vaccine vector based on polio virus has been facilitated because of the immense knowledge available about the virus. The complete viral RNA genome has been sequenced and the viral proteins identified. (Kitamura, 1981) (Racaniello, 1981) An infectious cDNA of the viral genome has been generated, making it possible to manipulate the virus genetically. (Racaniello, 1981) (Semler, 1984) The three dimensional structure of the complete virus is known and the major antigenic epitopes have been identified on the molecular level. (Hogle, 1985) The receptor (PVR) that polio virus utilizes to gain entry into the cells has been cloned and the nucleic acid sequence has been determined. (Mendelsohn, 1989; Ren, 1992) Furthermore, transgenic mice have been bred with expressed polio virus receptor and are therefore susceptible to polio virus infection. Therefore, an animal model exists to study recombinant polio virus vectors with all diseases, especially HIV disease.

The vast information available on the polio virus makes it an ideal target for the development of recombinant poliovirus/HIV vectors. Since poliovirus vaccines can be administered to mucosal sites and since polio replicates in Peyer's patches after initially inoculating tonsillar tissue, recombinant polio vaccines are a preferred embodiment for recombinant viral vaccines for HIV disease.

The availability of an infectious polio virus cDNA has prompted further investigation into the regions of the polio virus genome that can be deleted without compromising the replication capacity of the RNA. (Racaniello, 1981) (Semler, 1984) These RNA molecules or replicons retain the property for self-replication when introduced into cells. Early studies by Kaplan and Racaniello describe polio virus replicons with deletions encompassing the majority of the P1 region. (Kaplan, 1988) Polio virus replicons containing fragments of up to 1.5 kb of the HIV-1 gag, pol or env genes have been the subject of laboratory investigations. (Choi, 1991) The foreign genes were inserted so the translational reading frame was maintained between the remaining capsid sequences encoding the P2- and the P3-proteins. Transfection of these RNAs into cells resulted in the replication of these genomes as well as the expression of foreign proteins as a fusion protein with the flanking capsid proteins. (Kiyono, 1996)

The polio virus cDNA has been modified to accommodate larger genes for expression of recombinant proteins. In these vectors the complete P1 region of the polio virus was deleted, and a replicon was constructed which contained the complete gene for HIV-1 gag (approximately 1.5 kb). Transfection of this replicon into cells resulted in the production of the HIV-1 Gag precursor protein, $Pr55^{gag}$ which was eluted from the supernatant of the cells after centrifugation and visualized with electron microscopy. (Porter, 1996) (Kiyono, 1996)

In conclusion, it is possible to express a wide variety of foreign genes including genes encoding glycosylated proteins using the polio virus replicon system. (Kiyono, 1996)

C.2.4 mRNA Expression

The activation of a host cell results in HIV transcription of viral DNA into messenger RNA (mRNA). In HIV, viral RNA acts as both a messenger and genomic RNA. The viral DNA is transcribed into mRNA. The viral mRNA migrates into the cytoplasm where it becomes associated with cellular ribosomes and cellular transfer RNA to produce viral protein. Messenger RNA is a stable strand of genetic material that communicates the genetic information of the virus. Messenger RNA is attractive for use in an immunogenic composition for its stability and efficiency. Messenger RNA is more efficient than DNA in coding for protein.

RNA or DNA encodes for various proteins. An intermediate step is the production of mRNA. The mRNA for a protein or group of proteins is identical to the DNA strand (or RNA strand) encoding for it, with the exception that thymidine in DNA is substituted for uracil in RNA. Also in DNA the sugar moiety is deoxyribose in RNA the sugar moiety is ribose. The mRNA undergoes the process of capping where at the 5' end a 7-methylguanosine triphosphate is added and at the 3' end a poly(A)tail of about 100 bases is added to the untranslated segment of the 3' end. The cap is necessary for the proper binding of the ribosome and the tail signals an end to the ribosomal translation. Transcription is the process where DNA "transcribes" into mRNA. Translation is the process where mRNA is "translated" into proteins.

There are many theoretical advantages to mRNA within an immunogenic composition. These include but are not limited to: (1) mRNA does not need to cross through the nuclear membrane; (2) mRNA does not need to enter nucleoplasm; (3) mRNA does not need to integrate into host DNA; (4) mRNA does not need to undergo the process of transcription; (5) the host translational enzymes and ribosomes are available to the mRNA within the cell cytoplasm to allow for translation of the mRNA into protein; (6) a quicker immune response should be noted with mRNA in comparison to intracellular DNA because many steps in the production of viral protein are circumvented; (7) mRNA can be re-used several times so that many protein sequences can be translated from one mRNA template; therefore only minute quantities of mRNA need enter into the cell cytoplasm; and (8) because the intracellular production of proteins will be accomplished with mRNA, these proteins will be associated with MHC class I proteins on the cell surface and will elicit a $CD8^+$ cytotoxic T cell response.

The production of mRNA is straightforward. With the knowledge of a specific amino acid sequence of a specified HIV protein the RNA sequence complementary to this can be deduced. Then the RNA sequence can be capped and tailed at the 5' and 3' ends respectively. Furthermore mRNA can be produced by automated nucleic acid sequencing synthesis, as is known in the art.

C.2.5 Enhancing CD8+ T Cell Response for Naked DNA/RNA based Compositions

DNA-based compositions may offer a number of potential advantages over conventional vaccines. Single dosing, long-lasting immunity, cell-mediated immunity as well as humoral responses can be realized with intracellular production of viral particles introduced by recombinant DNA technology. In contrast subunit vaccines based on proteins internalized by endocytosis generally do not sensitize cells for $CD8^+$ T cell recognition.

Figure 6:
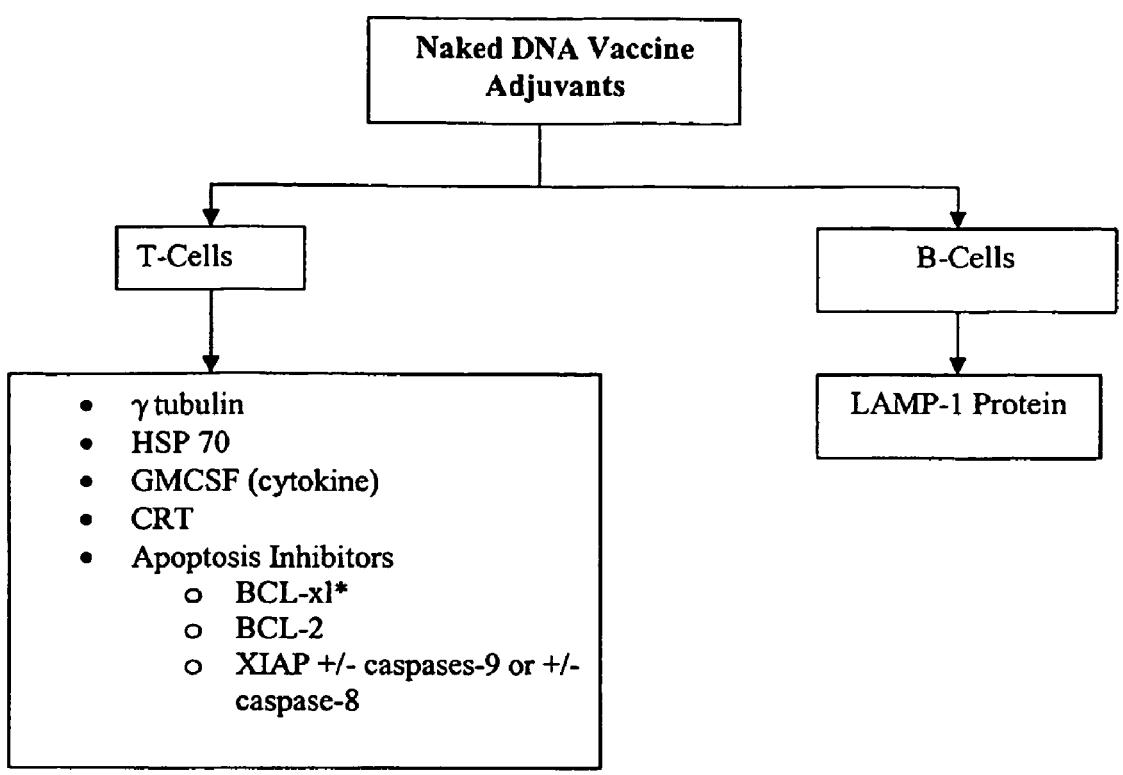
FIG. 6 is a list of immune stimulants for use with naked DNA compositions

One evasion strategy of HIV and other viral pathogens is to penetrate and replicate in non immunologic cells For example, epithelial cells are invaded by *Chlamydia* sp. and *Rickettsia* sp., while hepatocytes are targets for *Plasmodium* sp. and *L. monocytogenes*. As described above, although HIV targets primarily CD4 cells, other non immunologic tissues are invaded, such as the central nervous system. In stimulating an enhanced CD8 cytotoxic response, a broader scope of target cells may be recognized by the immune system. As described above, $CD8^+$ T cells recognize antigens in the context of MHC class I molecules that are present on all nucleated cells and enables the $CD8^+$ T cells to detect infected host cells of any type. In contrast, $CD4^+$ T cells are restricted to MHC class 2 expressing host cells and are thus much more limited in scope. Macrophages, dendritic cells and B cells bear MHC class I as well as MHC class II molecules. Furthermore, Langerhans cells of the skin possess both class I and class II MHC proteins. (Kaufmann, 1996) Accordingly, constituents enhancing CD8+ T cell response are contemplated for the present invention. As shown in FIG. 6, a variety of constituents may be combined to naked DNA/RNA embodiments (SEQ ID NOS: 2-3) to enhance CD8+ T cell response, some of which are described here.

For example, it has been demonstrated that specific hypomethylated CpG motifs within bacterially derived DNA can exhibit a potent adjuvant effect that is, in part, responsible for induction of Th1-type response that is a characteristic feature of DNA based vaccines. A significant feature of DNA based vaccines, unlike most conventional vaccines, is the unique ability to stimulate humoral and cell mediated responses in immunized animals. The ability to induce a potent Th1-type immune response is of considerable importance because with many pathogens (viral, bacterial, and parasitic), cell-mediated immunity and not the presence of antibodies is correlated with protection. (Lewis, 1999)

An additional method of enhancing cytotoxic T cell activity is to link the *mycobacterium tuberculosis* heat shock protein 70 (HSP70) to actual naked DNA/RNA that encodes the subunit. HSP70 is a cytosolic HSP that functions in protein folding, transfer, and degradation. (Chen, 2000) HSP reactive T cells can exert a strong helper effect by reacting to conjugated peptides; HSP can induce a T-helper pro-inflammatory response and induce the secretion of TNF-α and IFN. (Chen, 2000) Immunologically, calreticulin (CRT), a $Ca^{2+}$ binding protein located in the endoplasmic reticulum, is related to HSPs It associates with peptides delivered to the endoplasmic reticulum by transporters associated with antigen processing and presentation. (Wen-fang Cheng, 2002) CRT enhances CD8 activity.

Proteasomal degradation of antigen can enhance MHC class I presentation. (Chien-fu-hung, 2003) Thus, an additional method of enhancing cytotoxic T cell activity is to link gamma-tubulin to the DNA/RNA sequence. A centrosome is a sub-cellular compartment rich in proteasomes. Centrosomes are important in mitosis and the production of tubules. Centrosomes are also an important locus for MHC Class I antigen processing. Linking gamma-tubulin to DNA/RNA will result in cellular localization of the protein to the centrosomes, enhancing CD8+ T cell immune response. (Chan, 2000) Similarly, the present composition may use a DNA/RNA sequence encoding for the lysosome associated membrane protein (LAMP-1) linked to a DNA/RNA sequence for the matrix protein to enhance B-Cell response. (Chen, 2000) (Chien-fu-hung, 2003)

C.2.6 Enhancing CD8+ T Cell Response for Subunit Based Compositions

As noted above, subunit protein vaccines may not sensitize cells for $CD8^+$ T cell recognition. However priming of CTL responses with intact proteins has been achieved by incorporation of the antigen into immunostimulating complexes such as ISCOMs (a matrix of lipid micelles containing viral proteins that deliver antigens to the cytosol and allows induction of cytotoxic T cells) or liposomes. Furthermore cationic lipids have been used to enhance class I MHC pathways of antigen presenting cells in animals. One cationic lipid used is DOTAP (N-[1-(2,3-dioleoyloxy)propyl]-N,N,N-trimethylammonium methyl sulfate) which is a commercially available cationic lipid used for DNA transfection. Other cationic lipids which can sensitize target cells are available commercially. These lipids are similar in structure to DOTAP with two long hydrophobic alkyl chains coupled to one or more positively charged ammonium groups. The proposed mechanism of action for the cationic lipids involves an interaction between the macromolecule-lipid complex carrying an overall positive charge and the negatively charged cell surface followed by fusion with the cell membrane. In contrast, pH sensitive liposomes are thought to destabilize upon contact with the acidic environment of the endosome and rupture and/or fuse with the endosomal membrane to release their contents into the cytoplasm. (Walker, 1992)

ISCOMs contain Saponin which is a complex glycoside found in plants. Saponin possesses an adjuvant quality. Saponin has a hydrophilic oligosaccharide sequence of about 8 to 10 monosaccharides. The preparation of ISCOMs is know to those familiar with the art. Since ISCOMs also possess a steroid or triterpene their basic structure is amphiphatic. This allows ISCOMs to form a lipid matrix associated with hydrophobic proteins. The lipid quality of ISCOMs allows membrane fusion with a target cell. The proteins suspended in lipid matrix of the ISCOMs become internalized in the target cell and are subjected to immunologic clearance. (Kiyono, 1996)

Formation of complexes between the soluble protein of a subunit vaccine and DOTAP occurs by ionic interactions between the negative charge of the protein and the cationic lipid. Thus the maturation or modification of a subunit vaccine is not required. Association therefore requires only mixing of the subunit protein in the DOTAP solution or other cationic lipid prior to application to cells or injection into experimental animals or humans. Thus cationic lipids are readily available delivery vehicles for study of intracellular events that lead to class I MHC presentation of antigen and they can serve as an alternative to recombinant viruses for enhancing $CD8^+$ T cell response to viruses. (Walker, 1992)

The ISCOMs or lipid carriers act as adjuvants but with minimal toxicity. They load proteins and peptides into the cell cytoplasm allowing class I restricted T cell responses to peptides. Therefore they can be used with subunit vaccines to enhance CD8 activity. To gain access to the cytoplasm of the cell, the lipid micelles of the ISCOMs fuse with the cell membranes as noted above, and the particles trapped within the ISCOMs can be transported to the endoplasmic reticulum. Once inside the endoplasmic reticulum, these particles are bound to newly synthesized MHC class I molecules. For final protein modification the particles pass through the Golgi apparatus. They are then transported to the cell surface as peptide MHC class I complexes. (Parham, Peter, The Immune System, Ch. 12 (2004))

Therefore, the present composition should preferably be incorporated into ISCOMs, liposomes, and/or dissolved in cationic lipids to enhance T cell activity or to prime the CTL responses C.3. Conclusion—Method of Preparation Thus, the present invention comprises both a protein (SEQ ID NO: 1) based composition and a nucleic acid (SEQ ID NOS: 2-3) based composition that could be used to induce an immune response against the amino terminal end of the matrix protein (p17MA) and the covalent binding site for myristate (SEQ ID NOS: 1-3) on the HIV virus, and to create immune memory thereto. Nucleic acid based compositions may be DNA, RNA, or mRNA (SEQ ID NOS: 2-3). Recombinant nucleic acid carriers may be bacterial or viral. Preferably, the composition includes one or more constituents for enhancing CD8+ T cell response.

Protein based compositions (SEQ ID NO: 1) may be developed and administered using methods that are known in the art. For the purposes of compositions or vaccines that are based on nucleic acids and are administered to animals, then commercially available gene guns are a preferred method for delivery. This technique utilizes an instrument designed to propel DNA-coated gold particles directly into cells within the epidermis and dermis. DNA enters directly into dendritic cells, which leads to direct priming of CD8+ T cells. (Chen, 2000) In particular, gene gun delivery by DNA coated gold beads may thus be preferable for use with composition constituents enhancing CD8+ T cell immune response for nucleic acid based subunit compositions. (Chien-Fu Hung, 2003) Routes of administration for nucleic acid based compositions are summarized in FIG. 7 and below.

D. Description of Additional Alternative Embodiments and Immune Stimulants

The immune response contemplated by the present invention may be enhanced by the use of non-specific or specific substances stimulating immune response. The present invention may be mixed with appropriate immune stimulant or adjuvant, including those described as alternative embodiments below. Such compositions may be used as appropriate for the application. Customary stimulants or adjuvant known in the art include incomplete Freund's adjuvant, liposomes, etc. A preferred embodiment includes one or more stimulant taken from customary adjuvants and/or those compositions described further herein. In addition, DNA enhances complement activity and therefore, may be used concurrently as a DNA vaccine and an adjuvant. (The DPT vaccine is composed of three separate vaccine particles. The pertussis component acts as an adjuvant for the other two. (Parham, 2004) An analogous situation exists here, where a DNA vaccine (preferably encoding the sequence for the amino terminal end of the matrix protein (p17MA) and the covalent binding site for myristate (SEQ ID NOS: 2-3) on the HIV virus) for HIV disease would act as an adjuvant for a amino terminal end of the matrix protein (p17MA) and the covalent binding site for myristate (SEQ ID NO: 1) on the HIV virus subunit vaccine.)

To enhance immunogenicity of a recombinant bacterial or viral vector sialic acid needs to be removed from the plasma membrane of the bacteria or the protein coat and or envelope (if virus is enveloped) structure of the virus. Treatment with neuraminidase would effectively remove sialic acid residues without altering the protein structure of the bacteria or virus.

In an alternative embodiment, the composition may be bound covalently or otherwise to polysaccharides composed of mannose or mannan. Binding or coupling may be accomplished using methods known to those in the field. Mannose is a sugar found only on microorganisms and pathogens not ordinarily found within the human body. Mannose binding protein (MBP) is a collectin, a C-type lectin that contains regions of collagenous structure. It is present in normal human serum and consists of subunits each composed of three polypeptide chains, forming a collagen-like triple helix and three C-terminal globular carbohydrate recognition domains (CRDs). Six subunits together form an overall structure resembling the bouquet of tulip-like structure of C1q of the classical complement pathway. Binding of MBP to carbohydrate initiates the classical complement pathway to the activation of $C1r_2$ $C1s_2$. This may result in complement killing either directly through insertion of the terminal membrane attack complex or through opsonization by deposition of complement on the microbial surface. MBP may also activate C2 and C4 via another newly described serine protease called MASP (1 and 2) serine proteases. Thus, MBP also exhibits complement independent opsonizing activity, probably mediated by binding of the collagenous stalks to the collectin receptor of phagocytic cells. (Presanis J. S., et al., Biochemistry and Genetics of Mannan-binding Lectin (MBL), Biochemical Society Transactions, Vol. 31, pp 748-752 (2003) Any organism with mannose or mannan on its surface will stimulate the lectin pathway of complement activation. A composition bound to such polysaccharides will bind with mannose binding lectin in the serum, activating the lectin pathway of the complement system. Thus, this alternative embodiment would thereby enhance the overall immunologic response to the vaccine.

In another alternate embodiment, the composition may be combined with substances that stimulate or activate the alternative complement pathway. For example, it is known that certain forms of teichoic acid are potent activators of the alternative complement pathway. (Winkelstein J. A., J. of Immun., Vol. 120, pp 174-178 (1978)) In addition, zymosan, which may be derived from yeast cells, can induce cytokines and stimulate immune response in conjunction with the alternative pathway of the complement system. Zymosan is phagocytosed by macrophages with or without opsonization, and therefore has a useful immunologic property of activating the alternative pathway of complementation. The zymosan macrophage interaction is believed to enhance the Th-1 response. CD4 cells can be divided into Th-1 and Th-2 cells. Th-1 cells activate cytotoxic T cells by producing IL-2; whereas Th-2 cells activate B-cells by producing primarily IL-4 and IL-5. The level of Th-1 response produced by zymosan is regulated by C3 cleavage fragments, C3b and iC3b. The amplified C3b deposits on the accepted surface of zymosan and assembles macrophages, dendritic cells or other antigen-presenting cells. Macrophages, dendritic cells, and antigen-presenting cells make an antigen presentation to Th-1 cells after opsonizing zymosan, and after antigen-specific macrophage activation occurs. (Fearon D. T., et al., Proc. Natl. Acad. Sci, Vol. 74, pp 1683-1687 (1977)) Zymosan can therefore be used as an adjuvant; it enhances both humoral and cell-mediated immune responses to HIV disease. Thus, the composition may be bound covalently or otherwise to substances that stimulate the alternative complement pathway, such as teichoic acid or zymosan.

The adjuvant effect of zymosan on HIV specific DNA vaccine was demonstrated recently using a plasma vector (pCMV160 IIIb). In laboratory mice the plasmid vaccine was inoculated with and without the zymosan. Higher levels of both humoral immune response and HIV specific delayed type hypersensitivity (DTH) response were observed when zymosan was co-inoculated with the plasmid vector as to that using the plasmid vector alone. HIV specific cytotoxic T cell lymphocyte activity was also enhanced. The effects are suggested to be based on the consequences of its (zymosan) recruitment and activation of macrophages, dendritic cells, or antigen-presenting cells through complement activation and especially through the alternative pathway. These results suggest zymosan as an effective immunologic stimulant. (Ara, 2001)

Therefore, to enhance the immunogenicity of the composition, mannose, teichoic acid, zymosan, or some combination thereof may be bonded to the protein component of the subunit vaccine. Preferably, the polysaccharides will consist of sixteen separate saccharide units. (Pangburn, Michael K., Immun., Vol. 142, pp 2766-2770 (1989)) The preferred source for the carbohydrate/adjuvant component of the subunit vaccine would be the capsular polysaccharide of the yeast cell, *Cryptococcus neoformans* serotype C. (Sahu Arvind, et al., Biochem. J., Vol 302, pp 429-436 (1994)) This yeast cell exhibits four branching xylose sugars from each trimannose repeat unit. The thioester site of the C3 complement component demonstrates a strong preference for this specific carbohydrate sequence. This results in the cleavage of C3 into the C3a fragment and C3b. The C3b molecule is a focal point in all three complement pathways.

Additionally, all glucose molecules and polysaccharides are to be removed from the composition. The addition of insulin to a cell culture will facilitate the transport of extracellular glucose across the plasma membrane and into the cytoplasm of the cells. Free soluble glucose molecules inhibit both the rate and the extent of C3b deposition. (Sahu Arvind, 1994)

In an alternate embodiment, the effect of heparin may be inhibited. Heparin is a cofactor necessary for effective Factor H function. (Maillet, Francoise, et al., Mol. Immun., Vol. 25, pp 917-923 (1988)) (Maillet, Francoise, et al., Molecular Immun., Vol. 20, pp 1401-1404 (1983)) Further, CypA uses heparin as a binding partner when binding to host cells. (Saphire, Andrew C. S., et al., European Molecular Bio. J. 18:6771-6785 (1999)) As noted above, Factor H is a major limiting protein in the alternative complement pathway. The alternative complement pathway is the first arm of the immune system to respond to microorganisms or vaccines. Protamine binds heparin and is used to reduce the effective heparin in patients undergoing anticoagulation. (Furie, Bruce, Oral Anticoagulant Therapy, Hematology Basic Principles & Practice, Ch. 121 (3rd ed. 2000)) Recently, a less toxic heparin antagonist, low molecular weight protamine (LMWP) has become available. Protamine, or preferably LMWP for this embodiment, may be included as a component of the composition in order to impair the activity of Factor H in limiting the alternative complement pathway. (Liang J. F, et al., Biochemistry, Vol. 68, pp 116-120 (2002)) Alternatively, Heparinase is known to degrade Heparin enzymatically.

Branched partially hydrolyzed polysaccharides of glucose known as dextrans have been used for effective plasma expanders. (Hoffman, Ronald, Hematology Basic Principles and Practice, 2177 (3rd ed. 2000)) Dextran sulfate is a sodium salt of sulfuric acid esters of the polysaccharide dextran. Soluble dextran sulfate with a molecular weight greater than $5\times10^3$ is an inducer of the alternative pathway of complement. The number of sulfate groups per hundred glucose residues in the dextran determined the activation potency of the dextran in the alternative pathway. The optimal degree of sulphation was 50-60 $SO_4$/100 glucose molecules. (Burger, R., et al., Immunology, Vol. 29. pp 549-554 (1975))

Sulphated sephadex (SS) is a cross-linked insoluble form of dextran. Like soluble dextran sulphate SS activate the alternative pathway of complement and the classical pathway as well. Three variables control the activity of SS with both pathways of complement activity:

(1) Amount of sulphation; the higher the sulphated content up to 15.6% by weight resulted in higher complement activation. No complement activation was noted with sulphate content less than 2.43%;

(2) Concentration of SS; higher concentrations result in complement activation with a maximum C3 turnover at 40-50 μg/ml; and (3) Temperature; maximum C3 turnover was noted at 37° C. with a total loss of activity at 4° C.

(Burger, R., et al., Immunology 33:827 (1977)) Both soluble and insoluble forms of dextran (>5000 molecular weight) activate the alternative pathway of complement. This is accomplished by blocking the effect of factor H. (Burger, R., et al., European J. Immunology, pp. 291-295 (1981)) Low molecular weight dextran sulfate (<5000) enhances factor H binding therefore it limits the activity of the alternative pathway of complement. (Seppo Meri, et. al., Proc. Natl. Acad. Sci, Vol 87, pp 3982-3986 (1990) DNA like heparin also increases factor H binding. (Gardner, William D., Biochemical and Biophysical Research Communications, Vol. 94, pp 61-67 (1980))

Therefore, to enhance immunogenicity dextran sulfate with a molecular weight >5000 with 50-60 $SO_4$/100 glucose molecules may be included in the compound. Likewise SS with 15.6% $SO_4$ by weight at a concentration of 40-50 µg/ml at a temperature of 37° would enhance the immunogenicity of the compound. Low molecular weight dextran would not be included in the formulation since it would increase factor H binding and decrease complement activation.

In a further alternate embodiment, substances that stabilize C3 convertase may be used with the present invention. All three complement pathways lead to the production of C3b, which bonds covalently to the surface of microorganisms or components of the microorganisms presented in such an immunogenic composition. C3b is produced by enzymes known as C3 convertase. Cobra venom factor (CVF), derived from the snake Naja kaouthia stabilizes this enzyme. (Alper, C. A., et al., Science, Vol. 191, pp 1275-1276 (1976) The half life of CVF,C3b,Bb C3/C5 convertase is seven hours, in contrast to that of endogenously produced alternative complement pathway C3 convertase (C3b,Bb), which is 1.5 minutes. C3b,Bb is disassembled by Factor H and C3b is inactivated by the combined action of Factor H and Factor I. In contrast Factor CVF,C3b,Bb is resistant to all regulatory complement proteins. (Kock, Michael A., et al., J. of Biol. Chemistry, Vol. 279 pp 30836-30843 (2004)) C3b,Bb requires additional C3b to act on C5 whereas CVF,Bb can cleave C5 directly. Therefore, the CVF,Bb enzyme continuously activates C3 and C5. (Kock, 2004)

The biological function of CVF in cobra venom is believed to facilitate the entry of the toxic venom components into the bloodstream. This is achieved by complement activation causing release of the anaphylatoxins C3a, C5a and Bb, which increase vascular permeability. (Vogel, Carl W., Immunoconjugates, Ch. 9 (1987)) CVF, despite its derivation from cobra venom, is a non-toxic protein; CVF can be isolated from the other enzymes, polypeptides, etc., from cobra venom, which includes toxins.

Thus, administration of CVF results in an explosive production of C3b. (Vogel, 1987) (Kock, 2004) FIG. 8 illustrates the structural homology between C3 and CVF. C3b on the surface of microorganisms is recognized by follicular dendritic cells within the lymph nodes as well as T cells and B cells in the peripheral circulation and within the germinal centers of the lymph nodes. C3b is a powerful opsonin. Opsonins trigger several arms of the immune system simultaneously. (Hoffman, Ronald, Hematology Basic Principles and Practice, Ch. 27 (3rd ed. 2000)) Thus, in an alternative embodiment, CVF may be used as a component of the composition.

The preferred form of CVF is dCVF (De-α-galactosylated CVF). (Gowda, D. C., et al., "Immunoreactivity and function of Oligosaccharides in Cobra Venom Factor," J. of Immun., pp. 2977-2986, (Dec. 21, 1993)) Naturally occurring CVF is characterized by an unusual polysaccharide which is a fucosylated biantennary complex-type N-linked chain containing an α-galactosylated Le$^x$ antigenic epitope, Galα1-3Galβ1-4 (Fucα1-3) GlcNAcβ1. Removal of this polysaccharide can be accomplished by incubating CVF with peptide-N-glycosidase F (N-glycanase) at 37° C. for 18 to 23 hours at a ph of 8.0. Removal of this novel polysaccharide from CVF is necessary since 1% of human IgG reacts with the terminal Galα1-3Galβ1 sequence of CVF. However removal of this polysaccharide does not interfere with the complement fixation character of the molecule nor does it result in a shorter half life of the molecule. dCVF will be covalently bound to the polysaccharide unit(s) comprising the immunogenic composition.

In another embodiment, nickel compounds may be added to the composition. It has been shown that nickel is effective in enhancing the C3 convertase activity of both the classic and the alternative complement pathways. (Fishelson, Z., et al., J. of Immun., Vol. 129, pp 2603-2607 (1982)) Average nickel intake for average adults is estimated to be 60 to 260 micrograms per day, with an environmental health reference dose of 0.02 milligram per kilogram body weight per day (mg/kg/d). (U.S. EPA, 1986) It is contemplated that the present invention would include Nickel preferable in the form of nickel chloride on the order of average daily intake well below the reference dose. Therefore, the present invention may be produced using nickel to enhance immune response.

E. Summary

To prepare the composition that constitutes the vaccine agent for the invention, it is possible to use known methods of purification, synthesis, or genetic engineering. Practitioners skilled in the art may isolate and purify a fragment, or prepare a sequence encoding the amino terminal end of the matrix protein (p17MA) and the covalent binding site for myristate (SEQ ID NOS: 1-3) on the HIV virus. Protein fragments, naked DNA/RNA, recombinant DNA/RNA, or messenger RNA may be incorporated into pharmaceutical compositions appropriate for the anticipated method of administration, such as carriers or excipients. An animal or subject for which an immune response according to the present invention is desired may be administered the composition; a therapeutically effective dose would be that amount necessary to reverse specific immune suppression, to the extent desired, and determined using standard means, such as Chromium Release Assay, Intracellular Cytokine Assay, Lympho-proliferative Assay (LPA), Interferon Gamma (IFN-gamma) ELISpot Assays, and MHC Tetramer Binding Assays. The MHC Tetramer Binding Assay is preferable. These same laboratory tests would be applied to measure the immune response of an uninfected subject.

The analysis and development of the immunogenic composition should incorporate a wide range of doses of inactivated particulate for evaluation. Animal trials should consider differences in size, species, and immunological characteristics; it is anticipated that immunological differences between humans and animals may relegate animal trials to toxicity analysis. Clinical trials will involve at least the standard three phase model, ranging from safety and dosage in a small population, safety and immunogenicity in a second phase of several hundred volunteers, to a large scale effectiveness phase. The clinical trials should include appropriate exclusionary criteria as is customary, such as exclusion for other immune suppression conditions, pregnancy, active drug use, etc. A starting dose for trials with subunit proteins (SEQ ID NO: 1) may be 10 micrograms/strain for juveniles and 20 micrograms/strain for adults. For naked DNA vaccines (SEQ ID NOS: 2-3) a starting dose of 1 microgram/strain for all ages would be appropriate.

Administration may be made in a variety of routes, for example orally, transbucally, transmucosally, sublingually, nasally, rectally, vaginally, intraocularly, intramuscularly, intralymphatically, intravenously, subcutaneously, transdermally, intradermally, intra tumor, topically, transpulmonarily, by inhalation, by injection, or by implantation, etc. Various forms of the composition may include, without limitation, capsule, gel cap, tablet, enteric capsule, encapsulated particle, powder, suppository, injection, ointment, cream, implant, patch, liquid, inhalant, or spray, systemic, topical, or other oral media, solutions, suspensions, infusion, etc. Because some of the first targets for infection with HIV are epithelial cells and Langerhans cells in the skin and rectal and vaginal mucosa, then a preferable embodiment of delivery is dermal combined with rectal and/or vaginal suppositories. HIV is contracted predominantly by rectal and vaginal intercourse. Therefore rectal and/or vaginal suppository administration of the vaccine would be the preferred administration methodology. In addition, the present invention may be combined with other therapeutic agents, such as cytokines, including natural, recombinant and mutated forms, fragments, fusion proteins, and other analogues and derivatives of the cytokines, mixtures, other biologically active agents and formulation additives, etc. Those skilled in the art will recognize that for injection, formulation in aqueous solutions, such as Ringer's solution or a saline buffer may be appropriate. Liposomes, emulsions, and solvents are other examples of delivery vehicles. Oral administration would require carriers suitable for capsules, tablets, liquids, pills, etc, such as sucrose, cellulose, etc.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. An immunizing composition comprising a recombinant attenuated self-replicating viral RNA replicon encoding a human immunodeficiency virus type 1 (HIV-1) matrix (MA) protein myristate binding site, wherein said binding site is encoded by a nucleic acid consisting of SEQ ID NO.: 3, and a pharmaceutically acceptable carrier, wherein said composition is capable of inducing an HIV-1-specific Th-1 immune response.

2. A composition according to claim 1, wherein said composition is combined with an immune stimulant.

3. A composition according to claim 2, wherein said immune stimulant is an adjuvant.

4. A composition according to claim 3, wherein said adjuvant comprises cobra venom factor in a form adapted to enhance production of C3b.

5. A composition according to claim 4, wherein said cobra venom factor is dCVF.

6. An immunizing composition comprising a first recombinant attenuated self-replicating viral RNA replicon encoding a human immunodeficiency virus type 1 (HIV-1) matrix (MA) protein myristate binding site, wherein said binding site is encoded by a nucleic acid consisting of SEQ ID NO.: 3, a second recombinant attenuated self-replicating viral RNA replicon encoding an immune stimulant, and a pharmaceutically acceptable carrier, wherein said composition is capable of inducing an HIV-1-specific Th-1 immune response.

7. An immunizing composition comprising a first recombinant attenuated self-replicating viral RNA replicon encoding a human immunodeficiency virus type 1 (HIV-1) matrix (MA) protein myristate binding site, wherein said binding site is encoded by a nucleic acid consisting of SEQ ID NO.: 3, a second recombinant attenuated self-replicating viral RNA replicon encoding an adjuvant, and a pharmaceutically acceptable carrier, wherein said composition is capable of inducing an HIV-1-specific Th-1 immune response.

8. A composition according to claim 1, wherein said attenuated viral RNA replicon is a polioviral replicon.

* * * * *

SEQUENCE LISTING

<160> NUMBER OF SEQ ID NOS: 3

<210> SEQ ID NO 1
<211> LENGTH: 10
<212> TYPE: PRT
<213> ORGANISM: Human immunodeficiency virus type 1

<400> SEQUENCE: 1

Gly Ala Arg Ala Ser Val Leu Ser Gly Gly
1               5                   10

<210> SEQ ID NO 2
<211> LENGTH: 30
<212> TYPE: DNA
<213> ORGANISM: Human immunodeficiency virus type 1

<400> SEQUENCE: 2
ggtgctcgtg cttctgtttt atctggtggt                                    30

<210> SEQ ID NO 3
<211> LENGTH: 30
<212> TYPE: RNA
<213> ORGANISM: Human immunodeficency virus type 1

<400> SEQUENCE: 3
ggugcucgug cuucuguuuu aucugguggu                                    30